US006803345B2

(12) United States Patent
Herold et al.

(10) Patent No.: US 6,803,345 B2
(45) Date of Patent: Oct. 12, 2004

(54) HERBICIDE MICROEMULSION-FORMING-CONCENTRATES, MICROEMULSIONS, AND METHODS

(75) Inventors: Anthony E. Herold, Greeley, CO (US); Richard A. Beardmore, Windsor, CO (US); Scott K. Parrish, Spokane, WA (US)

(73) Assignee: Platte Chemical Co., Greeley, CO (US)

( * ) Notice: Subject to any disclaimer, the term of this patent is extended or adjusted under 35 U.S.C. 154(b) by 0 days.

(21) Appl. No.: 10/103,455

(22) Filed: Mar. 21, 2002

(65) Prior Publication Data

US 2003/0148889 A1 Aug. 7, 2003

Related U.S. Application Data

(60) Provisional application No. 60/325,289, filed on Sep. 26, 2001, provisional application No. 60/325,342, filed on Sep. 26, 2001, provisional application No. 60/325,343, filed on Sep. 26, 2001, and provisional application No. 60/361,016, filed on Feb. 28, 2002.

(51) Int. Cl.[7] ................ A01N 25/02; A01N 37/00; A01N 39/02; A01N 41/04; A01N 57/02

(52) U.S. Cl. .................. 504/254; 504/255; 504/258; 504/320; 504/321; 504/322; 504/323; 504/324; 504/325

(58) Field of Search .............................. 504/254, 255, 504/258, 320, 321, 322, 323, 324, 325

(56) References Cited

U.S. PATENT DOCUMENTS

| | | | |
|---|---|---|---|
| 3,755,339 A | 8/1973 | McKendry | 260/295 R |
| 3,761,486 A | 9/1973 | McGregor | 260/294.9 |
| 3,937,826 A | 2/1976 | Harris | 424/219 |
| 4,445,925 A | 5/1984 | Young | 71/28 |
| 4,816,060 A * | 3/1989 | Steller et al. | 71/92 |
| 4,971,630 A | 11/1990 | Skaptason | 71/117 |
| 4,994,101 A | 2/1991 | Young | 71/83 |
| 5,118,338 A | 6/1992 | Moller | 71/86 |
| 5,189,414 A | 2/1993 | Tawara | 340/825.5 |
| 5,221,319 A | 6/1993 | Van Haften et al. | 504/144 |
| 5,268,352 A | 12/1993 | Dexter | 504/206 |
| 5,270,286 A | 12/1993 | Ong | 504/130 |
| 5,280,008 A | 1/1994 | Cahoy et al. | 504/116 |
| 5,288,692 A | 2/1994 | Young | 504/127 |
| 5,317,042 A | 5/1994 | Narayanan | 514/772 |
| 5,328,889 A | 7/1994 | Van Haften et al. | 504/106 |
| 5,416,067 A | 5/1995 | Van Haften et al. | 504/323 |
| 5,565,409 A | 10/1996 | Sato et al. | 504/127 |
| 5,668,085 A | 9/1997 | Forbes et al. | 504/206 |
| 5,707,928 A | 1/1998 | Baker | 504/139 |
| 5,994,271 A | 11/1999 | Ravetta et al. | 504/206 |
| 6,069,115 A | 5/2000 | Pallett et al. | 504/220 |
| 6,071,857 A | 6/2000 | Vogt et al. | 504/116 |
| 6,165,939 A | 12/2000 | Agbaje et al. | 504/105 |
| 6,180,563 B1 | 1/2001 | Ruegg et al. | 504/128 |
| 6,180,566 B1 | 1/2001 | Nielsen et al. | 504/206 |
| 6,187,715 B1 | 2/2001 | Narayanan et al. | 504/118 |
| 6,207,617 B1 | 3/2001 | Gillespie | 504/206 |
| 6,369,001 B1 * | 4/2002 | Jimoh | 504/118 |
| 2002/0107149 A1 | 8/2002 | Volgas et al. | |

FOREIGN PATENT DOCUMENTS

| | | |
|---|---|---|
| CA | 1225533 | 8/1987 |
| DE | 2 328 192 | 1/1974 |
| EP | 0 100 440 | 2/1984 |
| EP | 0 163 598 | 4/1985 |
| EP | 0 216 126 | 4/1987 |
| EP | 0 217 125 | 4/1987 |
| EP | 0 243 522 | 11/1987 |
| EP | 0334041 | 9/1989 |
| EP | 0 357 553 | 3/1990 |
| EP | 0 433 577 | 6/1991 |
| EP | 0 454 968 | 11/1991 |
| EP | 0 641 161 | 10/1996 |
| EP | 0 703 724 | 2/2002 |
| GB | 2 230 955 | 11/1990 |
| GB | 2267825 | 12/1993 |
| WO | WO 92/21686 | 12/1992 |
| WO | WO94/19941 | 9/1994 |
| WO | WO96/08150 | 3/1996 |
| WO | WO98/17109 | 4/1998 |
| WO | WO99/55155 | 11/1999 |
| WO | WO00/42847 | 7/2000 |
| WO | WO00/67571 | 11/2000 |
| WO | WO01/52650 | 7/2001 |
| WO | WO02/11536 | 2/2002 |

OTHER PUBLICATIONS

PCT/US02/08830 International Search Report.

PCT/US02/08787 International Search Report.

PCT/US02/08952 Annex to Form PCT/ISA/206, Communication Relating to the Results of the Partial International Search.

PCT/US02/08953 Annex to Form PCT/ISA/206, Communication Relating to the Results of the Partial International Search.

Milton J. Rosen, "Surfactants and Interfacial Phenomena," John Wiley & Sons, pp. 239–240 (1978).

Briggs et al., "Physico–chemical Factors Affecting Uptake by Roots and Translocation to Shoots of Weak Acids in Barley," *Pesticide Science*, vol. 19, pp. 101–112 (1987).

Wyrill, J.B. et al., "Glyphosate Toxicity to Common Milkweed and Hemp Dogbane as Influenced by Surfactants," *Weed Science*, vol. 25, No. 3 pp. 275–287 (May 1977).

Tomlin, C., Ed., The Pesticide Manual, Tenth Edition, p. 1338, (1995).

(List continued on next page.)

*Primary Examiner*—S. Mark Clardy
(74) *Attorney, Agent, or Firm*—Kagan Binder, PLLC

(57) ABSTRACT

Described are herbicide compositions, in particular, herbicide compositions that are prepared from microemulsions containing herbicide compound in acid form, and methods of their preparation and use.

24 Claims, No Drawings

OTHER PUBLICATIONS

Chemical Abstracts, Turner et al., "Complexing agents as herbicide additives," Weed Res., vol. 18, No. 4, pp. 199–207 (1978), CA 89: 158688.

Chemical Abstracts, McMullan, "Effect of adjuvant and acidifying agent on imazamethabenz efficacy," Can. J. Plant Sci., vol. 72, No. 4, pp. 1389–1392 (1992), CA 118: 207455.

Chemical Abstracts, Zsoldos et al., "Effects of ph changes on ion and 2,4–D uptake of wheat roots," Dep. Plant Physiol., pp. 77–80 (1978), CA 92: 192532.

Chemical Abstracts, Shone et al., "Absorption and translocation of 2,4–dichlorophenoxyacetic acid (2,4–D) by barley roots," Annu. Rep.—Agric. Res. Counc., pp. 32–33 (1973), CA 85:57935.

Chemical Abstracts, Sherrick et al., "Effects of adjuvants and environment during plant development on glyphosate adsorption and translocation in field bindweed," Weed Sci., vol. 34, No. 6, pp. 811–816 (1986), CA 106: 14601.

PCT/US02/08952 International Search Report.
PCT/US02/08953 International Search Report.

* cited by examiner

HERBICIDE MICROEMULSION-FORMING-CONCENTRATES, MICROEMULSIONS, AND METHODS

This application claims the benefit of U.S. Provisional Application Serial No. 60/325,289, U.S. Provisional Application Serial No. 60/325,342, and U.S. Provisional Application Serial No. 60/325,343, all filed Sep. 26, 2001, and the benefit of U.S. Provisional Application Serial No. 60/361,016, entitled "Herbicide Compositions Comprising Imidazolinone Acid, Methods of Preparation, and Methods of Use," having Attorney Docket No. UAP0008/US, filed Feb. 28, 2002.

FIELD OF THE INVENTION

The invention relates to herbicide compositions and their preparation and use, and in particular to methods and compositions relating to microemulsion-forming compositions that contain herbicide compound in acid form, to microemulsions and other herbicide compositions derived from the microemulsion-forming-compositions, and to the related methods of preparation and use.

BACKGROUND

Commercially available herbicide compositions include a very large variety of active herbicide compounds. Herbicide compositions can be prepared from a variety of different types of precursor compositions, and can be commercially available and used in a variety of different types of compositions, including compositions referred to as wettable powders, water dispersible granules, granules, aqueous solutions, water soluble powders, emulsifiable concentrates, oil-based flowables, concentrated emulsions, suspoemulsions, emulsions, suspensions, suspension concentrates, mixtures, dispersions, and microemulsions, as well as others. Any of these different types of compositions may have different advantages or disadvantages depending on what type of active ingredients the herbicide includes.

Examples of just a few available active herbicide compounds include those of the general class known as phenoxy herbicides, e.g., 2,4-dichlorophenoxyacetic acid (known as 2,4-D), MCPA acid, MCPP acid; those of the general class known as pyridine herbicides, (e.g., triclopyr, fluoroxypyr); those of the general class of benzoic acid herbicides, (e.g., dicamba acid); those of the general class of aryloxy phenoxy propionic acid herbicides, (e.g., fluazifop acid and quizolofop acid); water-insoluble diphenyl ether type herbicides (e.g., oxyfluorfen or acifluorfen); glyphosate compounds (e.g., in the IPA salt form); imidizole herbicide compounds (e.g., imazapyr or imazaquin); as well as others.

Active herbicide ingredients such as these and others can be prepared from and used in the form of solid and liquid compositions including, as mentioned above, different forms of emulsions, suspensions, suspension concentrates, mixtures, dispersions, and microemulsions, etc. With regard to the liquid forms, the active ingredient (herbicide compound) is generally suspended or dissolved in a liquid, with the active herbicide compound taking the chemical form of a salt or ester, depending on which form is either soluble or suspendable in such a liquid composition. Most herbicide compositions are prepared from an ester or salt form of a herbicide compound, or are prepared using a step to convert an acid form of a herbicide compound to a salt or an ester to be either miscible in water or emulsifiable in water for application, often with the assistance of organic solvent.

With microemulsion compositions in particular, earlier microemulsion work typically included the use of herbicide compounds in forms other than their acid forms, e.g., ester or salt forms, because the salt or ester forms were considered to be most easily dispersed or suspended in a microemulsion. Typical microemulsions also incorporated organic solvents to effect suspension or dissolution of the herbicide compound.

New forms of effective herbicide compositions are always desirable, especially those that show advantages in processing, application, environmental profile (e.g., volatility), or efficacy. And there is always a desire to prepare herbicide compositions that reduce or eliminate organic solvents.

SUMMARY OF THE INVENTION

The invention relates to the use of herbicide compounds existing in their acid forms, dissolved in one or a combination of surfactants to form what is referred to herein as a microemulsion-forming-concentrate, or "MFC." The MFCs and their derivatives can be useful as herbicide compositions. The MFCs are preferably relatively stable compositions that at a desired time can be mixed or diluted with water to form a microemulsion or other derivative for application to control plant growth either alone or in combination with other ingredients such as other herbicides or additives, such as acidifying agents.

The MFCs can generally be prepared by mixing a selected herbicide compound in acid form into a surfactant or a mixture of surfactants, with optional heating and agitation, and with optional organic solvent. Exemplary amounts of herbicide compound and surfactant can be in the range from about 10 to about 40 parts by weight herbicide compound in acid form, and about 60 to about 90 parts by weight surfactant. The MFC may include amounts of water and organic solvents, but preferred MFCs can be made with reduced, minimal, or no organic solvent, e.g., with no added organic solvent.

The MFCs can be directly applied as herbicide compositions, or, preferably, can be combined with water and optionally other ingredients such as another herbicide or an acidifying agent, and then applied to control plant growth. For example, depending, e.g., on the herbicide compound and other factors, from about 0.05 to about 7 parts by volume MFC may be diluted with about 93 to about 99.95 parts by volume water to form a microemulsion. Other ingredients such as acidifying agent or other herbicides may also be added.

If an acidifying agent is added to the MFC or the microemulsion, the acidifying agent can preferably be added in an amount such that the pH of the microemulsion is below the pKa of the herbicide compound of the microemulsion, so that herbicide compound will be present in acid form. The use of herbicide compounds in acid form has been found to be advantageous. For example, many herbicide compositions having active herbicide compounds in their acid form can be prepared efficiently, can show particularly good efficacy, and can be unaffected or less affected by hard water.

An aspect of the invention relates to a microemulsion-forming-concentrate comprising herbicide compound in acid form and surfactant, wherein the concentrate can be combined with water to form a microemulsion. Preferred microemulsion-forming-concentrates can consist of or consist essentially of herbicide compound in acid form and surfactant, optionally including such additives as anticorrosion agents, antifoam agents, water, and organic solvent.

Another aspect of the invention relates to a microemulsion-forming-concentrate consisting of herbicide compound in acid form and surfactant, with optional acidifying agent or additives as discussed herein, and with no added organic solvent or added water, wherein the microemulsion-forming-concentrate can be combined with water to form a microemulsion.

Another aspect of the invention relates to a microemulsion comprising herbicide compound in acid form, surfactant, and water.

Another aspect of the invention relates to a microemulsion comprising a microemulsion-forming-concentrate comprising herbicide compound in acid form and surfactant, combined with water to form a microemulsion.

Another aspect of the invention relates to a method of applying a herbicide composition. The method comprises: preparing a herbicide composition comprising a microemulsion comprising herbicide compound in acid form and surfactant; and applying the herbicide composition comprising the herbicide compound in acid form to a plant or field to control plant growth.

Another aspect of the invention relates to a method of applying a herbicide. The method comprises preparing a microemulsion-forming-concentrate comprising herbicide compound in acid form and surfactant; preparing a microemulsion from the concentrate by diluting the microemulsion with an aqueous solution, the microemulsion comprising herbicide compound in acid form; and applying the herbicide composition to a plant to control plant growth while the herbicide compound is in acid form.

Yet another aspect of the invention relates to a method of preparing a microemulsion-forming-concentrate. The method comprises combining herbicide compound in acid form with surfactant, with optional heat and optional agitation, to produce a concentrate that can be combined with water to form a microemulsion.

Still another aspect of the invention relates to a method of preparing a microemulsion. The method comprises preparing a microemulsion-forming-concentrate by a method comprising combining herbicide compound in acid form with surfactant to produce a concentrate that can be combined with water to form a microemulsion; and combining the microemulsion-forming-concentrate with water to form a microemulsion.

DETAILED DESCRIPTION

The invention relates to herbicide compositions in the form of microemulsion-forming-concentrates and derivatives thereof. The term "herbicide composition" refers to a composition that includes a herbicide compound. Herbicide compositions include microemulsion-forming-concentrates and derivatives thereof such as microemulsions or herbicide application compositions, each of which is discussed in more detail below. The term "microemulsion" ("ME") means a solution that contains an oil phase and water, wherein the oil phase is finely dispersed such that light passes through the microemulsion and the microemulsion may be opaque or clear in appearance. Microemulsions are a known type of composition, and are sometimes considered either as micellar solutions containing inverted micelles (hydrophobic tails oriented toward the external oil phase and hydrophilic heads in the inner core) with water solubilized in the inner core, or as emulsions containing tiny droplets of water surrounded by an interfacial film. See, e.g., *Surfactants and Interfacial Phenomena*, Milton J. Rosen, Page 239&240, John Wiley & Sons (1978).

Microemulsion-forming-concentrates or "MFCs" of the invention include a herbicide compound in acid form dissolved in surfactant, optionally water, optionally may but preferably do not include added organic solvent, and can be diluted with water to form a microemulsion. MFCs can typically be translucent, opaque, or even clear solutions.

Different classes of herbicide compounds and different specific herbicide compounds within these classes can be used to produce MFCs according to the invention. A large variety of such herbicide compounds are well known and commercially available, and one of skill will be able to identify useful combinations of herbicide compound and surfactant useful to prepare herbicide compositions according to the invention, based on the present description. Suitable herbicide compounds can include herbicide compounds that act as a pre-emergent or post-emergent systemic herbicide, and that can exist in an acid form that can be dissolved in surfactant, optionally with the use of water or organic solvent, to form an MFC. Compositions and methods of this invention are particularly beneficial when using herbicides having post-emergent activity, i.e., systemic herbicidal activity toward established plants, due to the improvements in post-emergent, systemic activity available with these compositions and methods. While wishing not to be bound by theory, it is believed that the use of a herbicide compound in acid form, especially applied directly to a plant, and especially in a herbicide composition having an acidic and a relatively low pH (e.g., below 7, 6, or 5, or below the pKa of a herbicide compound, or lower) can effect improvements in plant control by one or both of the following mechanisms. First, a charge-neutral molecule (such as an acid) can have an easier time penetrating a cuticle on a plant compared to a charged molecule (e.g., salt). Secondly, when the herbicide compound in acid form is applied with a herbicide composition containing an acidifying agent and at a low pH, the acidifying agent and low pH can have a damaging effect on a plant's surface, thereby allowing more herbicide compound to penetrate the plant surface. Also, the acid form of a herbicide compound, due to its uncharged state, can be advantageously less affected or unaffected by hard water, e.g., less susceptible to de-activation by hard water.

Herbicide compounds may typically be available in ester or salt forms, and many herbicide compositions are conventionally sold commercially to contain herbicide compounds in either a salt or ester form, which are often considered to be relatively soluble, dispersible, or emulsifiable in water, as opposed to acid forms which are often less soluble in water. Acid forms of herbicides are used according to the invention.

"Herbicide compound in acid form," herein refers to a herbicide compound that exists in a form of the compound that is considered to be the "acid" form of the compound, as opposed to a different chemical form of the same compound such as a salt or an ester form. Many herbicide compounds are capable of existing in discernible, understood, chemically-different forms, including, e.g., an acid form, an ester form, or a salt form. The term "herbicide compound in acid form" includes herbicide compounds of these types, when the compound is in the acid as opposed to an ester or a salt or other non-acid form.

One way of identifying a herbicide compound in acid form is to reference a pKa of a herbicide compound. The pKa of a herbicide compound is understood to refer to the negative logarithm (base 10) of the equilibrium constant K for the reaction of the herbicide compound between its acid form and its neutral form. Methods of determining the pKa for a herbicide compound will be readily understood by the skilled artisan. Exemplary herbicide compounds that are capable of existing in acid form can have a pKa below about 6, or below about 5 or 4. Some herbicide compounds include more than one acidic hydrogen and therefore have more than a single pKa value. According to the invention, the relevant and referred to pKa is the pKa of a herbicide compound that relates to the change of the compound between the compound considered to be the deprotonated "acid" form of the compound, and what is considered to be the protonated (neutral) form of the "acid" form. The protonated acid form predominates at pH below the pKa, and the deprotonated form predominates at pH above the pKa. Examples of exemplary pKa values for certain herbicide compounds are included in the Table 1.

Some examples of useful herbicide compounds that can be used in their acid forms to produce MFCs in surfactant include the following, some or all of which are commercially available in their acid form (though presently not generally sold in that form as herbicide formulations). For herbicide compounds that are sold in a form other than the acid form, such as a salt or ester form, a skilled chemist will understand how to convert the non-acid to an acid form for use as described herein.

The class of phenoxy herbicides generally includes herbicides derived from chlorinated phenols, and includes herbicide compounds that can exist in an acid form. Examples include the well known herbicides 2,4-dichlorophenoxyacetic acid (known as 2,4-D), 4-methyl-4-chlorophenoxyacetic acid (MCPA Acid), and 2(-2-methyl-4-chlorophenoxy)propionic acid (MCPP acid), as well as others.

Pyridine herbicides are herbicides derived from a pyridine ring-containing compound, and includes herbicide compounds that can exist in an acid form. Examples include 3,5,6-trichloro-2-pyridyloxyacetic acid (triclopyr acid) and fluroxypyr (4-amino-3,5-dichloro-6-fluoro-2-pyridyloxyacetic acid), as well as others.

Benzoic acid herbicide compounds include or are derived from benzoic acid compounds. This class of herbicide compounds includes herbicide compounds that can exist in an acid form. A single example is dicamba acid (3,6-dichloro-O-anisic acid), but others could also be used according to the invention.

Aryloxy phenoxy propionic acid herbicide compounds (also referred to sometimes as "oxyphenoxy" herbicides), are another class of herbicides that can exist in an acid form. Examples of specific compounds include fluazifop acid and quizolofop acid, as well as others.

TABLE 1

| Acidic Herbicides: | pKas | Trade Name | Salt Form | Herbicide Family | Sub Family |
|---|---|---|---|---|---|
| Bromoxynil | 4.06 | BUTRIL | | Benzonitrile | |
| Ioxynil | 3.96 | | | Benzonitrile | |
| Bentazon | NA | BASAGRAN | sodium | Non-Family | |
| Dicamba | 1.87 | BANVEL | diglycolamine diethylamine | Growth Regulator | Bezoic Acid |
| Diclofop | 3.57 | HOELON | | Aryloxyphenoxy-propionate | |
| Fenoxaprop | NA | PUMA | | Aryloxyphenoxy-propionate | |
| Fluazifop-p | 2.98 | FUSILADE | | Aryloxyphenoxy-propionate | |
| Fosamine | NA | KRENITE | | Non-Family | |
| Glufosinate | 2, 2.9 | LIBERTY | ammonium | Phosphorylated amino acid | |
| Glyphosate | 2.6, 5.6 | ROUNDUP | Isoproplyamine | Non-Family | |
| Haloxyfop | 4.33 | VERDICT | | Aryloxyphenoxy-propionate | |
| Imazamethbenz | 2.9 | ASSERT | | Imidazolinone | |
| Imazapyr | 2, 3 | ARSENAL | Isoproplyamine | Imidazolinone | |
| Imazaquin | 3.8 | SCEPTER | ammonium | Imidazolinone | |
| Imazamox | | RAPTOR | | Imidazolinone | |
| Imazethapyr | 3.9 | PURSUIT | ammonium | Imidazolinone | |
| Picloram | 2.3 | TORDON | triisopropanolamine | Growth Regulator | Pyridine |
| Triclopyr | 2.68 | GARLON | triethylamine | Growth Regulator | Pyridine |
| Clopyralid | 2.3 | STINGER | monoethanolamine | Growth Regulator | Pyridine |
| Floroxypyr | | STARANE | | Growth Regulator | Pyridine |
| Quinclorac | 4.34 | FACET | | Growth Regulator | Quinolinic Acid |
| Quizalofop-p | NA | ASSURE | | Aryloxyphenoxy-propionate | |
| Sethoxydim | 4.16 | POAST | | Cyclohexanedione | |
| 2,4-D | 2.8 | | sodium ammonium triethanolamine dimethylamine | Growth Regulator | Phenoxy Carboxylic |
| 2,4-DB | 4.8 | | | | Phenoxy Carboxylic |
| Dichlorprop | 2.86 | | dimethylamine | Growth Regulator | Phenoxy Carboxylic |
| MCPA | | | | Growth Regulator | Phenoxy Carboxylic |
| Mecoprop (MCPP) | | | | Growth Regulator | Phenoxy Carboxylic |
| Clethodim | | SELECT | | Cyclohexanedione | |
| Sethoxydim | | | | | |
| Acifluorfen | 3.86 | BLAZER | sodium | Diphenyl Ether | |
| Dacthal | | | | Phthalic Acid | |
| Endothal | | | | Phthalic Acid | |

TABLE 1-continued

| Acidic Herbicides: | pKas | Trade Name | Salt Form | Herbicide Family | Sub Family |
|---|---|---|---|---|---|
| Alanap | | | | Phthalic Acid | |
| Asulam | 4.82 | | | Non-Family | |

(Where a pKa is not listed, a skilled artisan would be able to identify the pKa.)

The herbicide compound in acid form is dissolved in surfactant (and optionally water and organic acid) to form an MFC that contains surfactant and dissolved herbicide compound in acid form.

A very large variety of surfactants are known and commercially available, including such different classes as cationic surfactants, anionic surfactants, non-ionic surfactants, ionic surfactants, and amphoteric surfactants. According to the invention, the surfactant can be any surfactant or combination of two or more surfactants useful to dissolve the herbicide compound in its acid form to produce a microemulsion-forming-concentrate.

Examples of some preferred surfactants include cationic, non-ionic, and anionic surfactants. Of these, some even more specific types of preferred surfactants include non-ionic linear or branched alcohol ethoxylate surfactants, anionic phosphoric acid ester surfactants (sometimes referred to as "phosphate ester" surfactants), and cationic ethoxylated tallow amine surfactants. Examples of surfactants and identification of their intermediate and general classifications are as follows:

thalene sulfonate, sodium dimethyl naphthalene sulfonate, and mixtures thereof. Sodium butyl naphthalene sulfonate is commercially available, for example, under the trade name "MORWET B" from Witco/Crompton, Greenwich, Conn. Sodium di-n-butyl naphthalene sulfonate is commercially available, for example, under the trade name "MORWET DB" from Witco/Crompton, Greenwich, Conn. Sodium diisopropyl naphthalene sulfonate is commercially available, for example, under the trade name "MORWET IP" from Witco/Crompton, Greenwich, Conn. Sodium dimethyl naphthalene sulfonate surfactant is commercially available, for example, under the trade name "SELLOGEN HR" from Henkle Corp., Cincinnati, Ohio.

An exemplary ethoxylated tristyrylphenol phosphate potassium salt surfactant is commercially available, for example, under the trade name "SOPROPHOR FLK" from Rhodia, Cranbury, N.J.

A nonionic surfactant is a surface-active molecule that does not contain ionizable polar end groups but does contain hydrophilic and lipophilic portions. Exemplary nonionic surfactants include polyoxyethylene alkylether or alk-

SURFACTANTS

| TRADE NAME | COMMON NAME | INTERMEDIATE CLASSIFICATION | GENERAL CLASSIFICATION |
|---|---|---|---|
| Tomadol 1-5 | 11 carbon 5 mole linear alcohol | ethoxylated linear alcohol | nonionic |
| Tomadol 1-7 | 11 carbon 7 mole linear alcohol | ethoxylated linear alcohol | nonionic |
| Surfonic L12-6 | 12 carbon 6 mole linear alcohol | ethoxylated linear alcohol | nonionic |
| Trymeen 6607 | 20 mole tallow amine | ethoxylated amines/amide | cationic |
| Stepfac 8170 | phosphate ester | phosphate ester | anionic |
| Surfonic PE 1218 | phosphate ester | phosphate ester | anionic |
| Surfonic DDA6 | 6 mole branched alcohol ethoxylate | branched alcohol ethoxylate | nonionic |
| Surfonic TDA6 | 6 mole tridecyl alcohol | branched alcohol ethoxylate | nonionic |
| Surfonic T-15 | 20 mole tallow amine | ethoxylated amines/amide | cationic |
| Surfonic OP-70 | 7 mole octylphenol | ethoxylated alkyl phenol | nonionic |
| Tergitol NP-6 | 6 mole nonylphenol | ethoxylated alkyl phenol | nonionic |
| Trylox 5902 | 16 mole castor oil | ethoxylated fatty acids/oils | nonionic |
| Span 80 | sorbitan laurate | sorbitan laurate | nonionic |
| Tween 80 | polysorbate 80 | sorbitan oleate | nonionic |
| Soprophor 796P | tristerol phenol EO/PO | propylated, ethoxylated fatty acid, alcohols, or alkyl phenols | nonionic |
| Surfonic L24-5 | 24 carbon 5 mole linear alcohol | ethoxylated linear alcohol | nonionic |

An anionic surfactant is a surface-active molecule in which an active portion of a lipophilic portion of the molecule forms a negative ion (i.e., anion) when placed in aqueous solution. Exemplary anionic surfactants include phosphoric acid ester surfactants (sometimes referred to as "phosphate ester" surfactants), sodium alkyl naphthalene sulfonate surfactants, and ethoxylated tristyrylphenol phosphate salts.

Exemplary sodium alkyl naphthalene sulfonate surfactants include sodium butyl naphthalene sulfonate, sodium di-n-butyl naphthalene sulfonate, sodium diisopropyl naphenylether surfactants. Nonionic surfactant used to prepare a suspension concentrate as described herein may include long or short chain alcohol ethoxylate surfactant. The alcohol ethoxylate surfactant may be branched or linear.

An example of a useful nonionic polyoxyalkylene surfactant includes alcohol ethoxylate having the general formula:

$$R-O-((CH_2)_xO)_y-H$$

wherein R may be "long" or "short" chain and "branched" or "linear" alkyl. R preferably can be a "short chain" branched or linear alcohol, meaning that it can have from about 3 to 23 or fewer carbon atoms. With respect to the oxyalkylene, x can preferably be in the range from about 2 to 5, preferably from about 2 to 4 (e.g., 2 or 3, for a polyoxyethylene or polyoxypropylene, respectively) and y can preferably be in the in the range from 5 to 25.

Examples of useful short chain nonionic polyoxyalkylenes include linear alcohol polyoxyethylenes having the general formula:

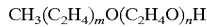

wherein $CH_3(C_2H_4)_m$ is a short chain linear alkyl having from about 3 to 23 or fewer carbon atoms (i.e., m can be in the range from about 1 to 11 carbon atoms), and n is in the range from about 5 to 25.

Another example is short chain nonionic polyoxypropylenes having the general formula:

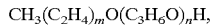

wherein $CH_3(C_2H_4)_m$ is a short chain linear alkyl having from about 3 to 23 or fewer carbon atoms (i.e., m can be in the range from about 1 to 11 carbon atoms), and n can preferably be in the range from about 5 to 25.

Exemplary short chain linear alcohol ethoxylate surfactant are commercially available, for example, under the trade names "SURFONIC L12-6" from Huntsman, Austin, Tex., "SURFONIC L24-7" from Huntsman, Austin, Tex., "TERGITOL 15-S-7", "TERGITOL 24-L-60", "ALPHONIC 1012-60", "ALPOHONIC 1414-60", "BIOSOFT ET 630, " from Stepan Company, Chicago, Ill., and "GENOPAL 24-L-60."

Other exemplary surfactants include polyethylene glycol, fatty acid ethoxylates, phosphate esters, octyl phenol ethoxylates, and nonyl phenol ethoxylates.

Useful polyethylene glycol surfactants are commercially available, for example, under the trade names "ADEKA PEG" from Asahi Denka Kogyo, Tokyo, Japan.

Useful fatty acid ethoxylate surfactants are commercially available, for example, under the trade names "NINEX MT-610", "NINEX MT-615", and "NINEX MT-630" from Stepan, Northfield, Ill.

Useful phosphate ester surfactants are commercially available, for example, under the trade names "STEPFAC 8180", "STEPFAC 8181", and "STEPFAC 8182" from Stepan.

Useful octyl phenol ethoxylate surfactants are commercially available, for example, under the trade name "MAKON OP-9" from Stepan, Northfield, Ill.

Useful nonyl phenol ethoxylate surfactants are commercially available, for example, under the trade names "MAKON 4", "MAKON 6", "MAKON 8", "MAKON 10", "MAKON 12", and "MAKON 14" from Stepan, Northfield, Ill.

A cationic surfactant is a surface-active molecule in which an active portion of a lipophilic portion of the molecule forms a positive ion (i.e., cation) when placed in aqueous solution. In one embodiment, exemplary cationic surfactant includes ethoxylated tallow amine.

Generally speaking, the amounts of surfactant and herbicide compound in the MFC can be any useful amounts, meaning that the amounts are sufficient to produce a useful herbicide composition or a useful herbicide composition precursor, based on the amount of herbicide dissolved in the surfactant. Amounts of either organic solvent or water may also be used to produce an MFC, but it is preferred that only small amounts or organic solvent and more preferably no organic solvent be added to the MFC. Useful relative amounts of herbicide and surfactant will vary for different herbicide compounds and different surfactants, as well as the optional presence of organic solvent or water. Exemplary MFCs can include from about 10 to about 40 parts by weight, e.g., from about 20 to about 35 parts by weight herbicide compound in acid form, and from about 60 to about 90, e.g., from about 65 to about 80 parts by weight surfactant.

The MFC may include water and organic solvents to facilitate dissolution of the herbicide compound. An exemplary amount of organic solvent may be below about 20 percent by weight e.g., below about 10 percent by weight, and an exemplary amount of water may also be below about 20 percent by weight, e.g., below about 10 percent by weight, for a total amount of water and organic solvent up to about 40 percent by weight. Preferred MFCs can be made with minimal or no amounts of water or organic solvents. Generally, small amounts or no amount of organic solvent or water can be preferred, such that the MFC contains substantially no organic solvent or water. Compositions described herein may include some amounts of organic solvent or water present due to processing history of ingredients used to produce the MFC, such as the preparation of a surfactant or herbicide compound using an organic solvent or water, but that amount of organic solvent or water will normally be less than 5 weight percent or less than 1 weight percent of the total MFC composition, e.g., less than 0.5 or 0.1 weight percent of the total weight of the MFC composition. "Substantially no organic solvent" means that a composition includes no added organic solvent, but may include residual organic solvent as noted. "Substantially no water" means that a composition includes no added water, but may include residual water as noted.

The MFC is preferably stable in the form of a microemulsion-forming-concentrate, for a useful period, meaning that the composition does not settle or otherwise transform out of the MFC form, and maintains the form of an MFC for a useful amount of time, after which the MFC can be diluted with water to form a microemulsion. Useful periods of stability can depend on the timing of dilution and application of the MFC following preparation of the MFC, which time period can vary greatly, e.g., based on convenience, preference, or other factors. If an MFC or derivative can be applied (typically following dilution) in a short or very short period of time after preparation of the MFC, any amount of longer-term stability is not required. Exemplary MFCs of the invention have been found to be stable at approximately room temperature and in substantially undisturbed and un-agitated environments for periods in excess of 6 or 12 months. Longer or shorter periods would also be useful.

The MFC can be applied directly to a field or plant to control undesired plant growth, or can be diluted with water to form a microemulsion, which, optionally with other ingredients as described below, can be applied to a field or plant as a "herbicide application composition" to control undesired plant growth. "Herbicide application composition" refers to a herbicide composition having a concentration of herbicide compound that would normally be applied to a field or plant to control undesired plant growth, as opposed, for example, to compositions having higher concentrations of herbicide compound that sometimes occur in preparation, storage, shipping, or sale of a herbicide composition. It is noted that any of the herbicide compositions described herein, such as the MFC, may be capable of controlling plant growth, e.g., if applied directly to a plant.

Yet it is typical for reasons of efficiency, cost, convenience, techniques presently used in applying herbicide compositions, and environmental considerations, to use a relatively diluted form of herbicide composition to conveniently apply a specific and known amount of herbicide compound per acre or per other unit of application. By way of example, herbicide application compositions include any herbicide composition having such a specific concentration of herbicide compound for application, e.g., to a field, and specifically include microemulsions prepared directly by diluting an MFC with water, and microemulsions or other solutions prepared by diluting an MFC with water and adding one or more other optional ingredients, as will be described in more detail below.

Relative amounts of MFC and water used to prepare a microemulsion can be any amounts that produce a useful microemulsion, and can depend on factors such as the composition of the MFC (e.g., the type and concentration of the herbicide compound), the intended application (including the plant to be controlled or the crop to be protected), the mode of application (e.g., field or aerial spraying or application from a hand-held spray applicator, or other technique), etc.

Although amounts outside of the following ranges can also be useful, and exact ratios can depend significantly on the identity of herbicide compound used, exemplary MFCs can be combined with water to form a microemulsion by mixing about 0.05 to about 7 parts by volume MFC with from about 93 to about 99.95 parts by volume water (e.g., 2 ml MFC to 98 ml water, 1 quart MFC to 12 gallons water, 12 oz. MFC to 20 gallons water, 0.065 parts MFC to 99.935 parts water, or equivalent amounts of each). The actual amount of MFC to water can vary depending on the crop, weed species, the amount of spray volume as chosen by the applicator, the desired strength of the application composition, or whether other ingredients are included or added. This composition may be applied as a herbicide application composition, optionally additionally including other ingredients such as a desired amount of acidifying agent or one or more other herbicide.

Additional ingredients can be included in the MFC or herbicide composition for purposes of stability, pH adjustment, anti-foaming, or to facilitate application or to increase efficacy. These other ingredients may be added to the MFC or herbicide application composition at any time and in any order, as desired and convenient. Exemplary additional ingredients include antifoaming agents, acidifying agents, anticorrosion agents, etc.

Antifoaming agents are well understood in the chemical and herbicide arts, and a variety of useful examples are commercially available. As is known, antifoam agents are substances, such as silicones, organic phosphates, and alcohols, which inhibit the formation of bubbles in a liquid during its agitation by reducing its surface tension. One specific example of a commercially available antifoam agent is SAG 10 (a 10% silicone in water antifoam), commercially available from Witco OSI. The amount of antifoaming agent used in an MFC or in a microemulsion will also be apparent to the skilled artisan, with typical amounts being less than 1 percent by weight, e.g., less than 0.5 percent.

A preferred embodiment of a herbicide application composition can further include an acidifying agent, particularly an acidifying agent that improves the efficacy of the herbicide composition. A variety of different acidifying agents can be useful with the herbicide compositions of the invention, e.g., to improve efficacy of a herbicide composition. Examples of a certain type of acidifying agent are described in U.S. Pat. Nos. 4,445,925, 4,994,101, 5,288,692, the disclosures of which are incorporated herein by reference. Other exemplary acidifying agents are known, and still others are described in Assignee's copending U.S. Patent Application entitled "Herbicide Composition Comprising Herbicide Compound in Acid Form and Acidifying Agent," having Attorney's Docket Number UAP0006/US/2, and Ser. No. _____, filed on even date herewith, and incorporated herein by reference. See also Assignee's copending U.S. Patent Application entitled "Herbicide Compositions Comprising Suspension Concentrate with Glyphosate Acid, Methods of Preparation, and Methods of Use," having Attorney's Docket Number UAP0007/US/2, and Ser. number _____, filed on even date herewith, and incorporated herein by reference.

The particular acidifying agent chosen and the amount used can be based on factors such as the intended application (including the identity of the undesirable plant growth, and the desired plant growth), the method of application, the herbicide compound chosen, physical and chemical properties of the herbicide application composition, and other factors. The acidifying agent may be any of a variety of suitable organic and inorganic acids, of any useful strength or concentration (e.g., concentrated or diluted), that can be added to an MFC or a microemulsion, etc., preferably without causing substantial or undue negative effects such as reaction with another ingredient such as the herbicide compound, precipitation, etc.

Non-limiting examples of specifically useful acidifying agents include acids such as sulfuric acid, phosphoric acid, hydrochloric acid, nitric acid, acetic acid (e.g., "glacial" acidic acid), perchloric acid, polyphosphoric acid, acidic adducts such as the sulfuric acid adducts described in U.S. Pat. No. 5,288,692 (Young), especially the adduct of sulfuric acid and urea, and any other acidifying agent that can be used to affect the pH of a herbicide composition. It will be understood that such acidifying agents can be used alone or in combination, and can be included in a herbicide composition in a concentrated or a diluted form.

One useful type of acidifying agent includes adducts of sulfuric acid and an "amide" according to the formula:

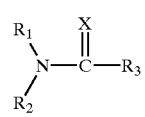

(1)

wherein X is chalcogen, and each of $R_1$, $R_2$, and $R_3$ is independently selected from hydrogen and organic radicals. As used herein, "amide" encompasses all compounds of formula (1) regardless of the chalcogen. The molar ratio of amide to acid is usually in the range of about ¼ to less than 2 so that at least some of the acid is present as the monoamide-acid adduct.

When $R_1$, $R_2$, and $R_3$ are organic radicals, they may be cyclic or acyclic, straight, or branched chained, and can contain one or more heteroatoms such as sulfur, nitrogen, oxygen, phosphorus and the like. Further, $R_1$, $R_2$, and $R_3$ can contain one or more substituents such as thiol, hydroxy, nitro, amino, nitrile, amide, ester and halogen groups and others. Such organic radicals may contain aryl groups such as aralkyl and alkaryl groups. Certain preferred organic radicals can be free of olefinic or alkynyl unsaturation and can generally have up to about 20, preferably up to about 10 carbon atoms. Particularly preferred amides include urea, thiourea, formamide, dimethylformamide, biuret, triuret, thioformamide, and combinations of these.

The chalcogens are elements of Periodic Group VI-B and include oxygen, sulfur, selenium, tellurium, and polonium. Oxygen and sulfur can be preferred due to low cost, availability, low toxicity, and chemical activity, and oxygen is the most preferred.

An example of a specific adduct of formula (1) is the sulfuric acid/urea adduct:

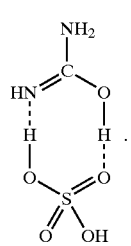

(2)

Other types of useful acidifying agents, as stated, include sulfuric acid, phosphoric acid, hydrochloric acid, nitric acid, acetic acid (e.g., "glacial" acidic acid), perchloric acid, polyphosphoric acid, other adducts, etc. Various such acids are commercially available in different forms and concentrations, including solids, liquid solutions, concentrated liquid solutions, etc., or can be prepared by one of ordinary skill. Any such form of acidifying agent may be useful to reduce the pH of a herbicide composition, preferably without causing any undue negative effect on the herbicide composition. Useful forms of these types of acidifying agents can include solid forms, liquid forms (aqueous forms), and concentrated liquid forms. The chosen form of an acidifying agent may be based on factors such as commercial availability, convenience, and the overall desired properties of the herbicide composition, its different ingredients (e.g., the herbicide compound), and its desired method of preparation and use.

The particular amount of acidifying agent added to an MFC, herbicide application composition, or other herbicide composition, can be selected depending on factors such as the particular herbicide composition and chemistry of the herbicide composition, including the amounts and chemistries of surfactant and herbicide compound; the amount and identity of any solvent; whether water is included and in what amount; the type of acidifying agent and its chemistry and strength (concentration); and based on the desired pH of the herbicide composition and the relevant pKa of the herbicide compound. As stated, preferred amounts of any particular acidifying agent can be capable of improving the efficacy of the herbicide composition, and particularly preferred amounts will be sufficient to produce an application composition having a pH below the relevant pKa of the herbicide compound.

Examples of useful amounts of acidifying agents will be quite varied, considering the above factors. Relatively strong concentrations of liquid (aqueous) acidifying agent solutions such as 93% liquid sulfuric acid, 72% phosphoric acid, 85% polyphosphoric acid, 90% nitric acid, 99% glacial acetic acid, etc., can be added directly or can be first diluted and then added to a herbicide composition in an amount to bring the pH to below about 7, e.g., below about 5 or 6, preferably below the pKa of the herbicide compound. In terms of volume percent, preferred amounts are highly dependent on the identity of the acidifying agent and the herbicide composition and its pKa. Very generally speaking, useful relative amounts of acidifying agent to microemulsion can be below about 5 or 10 volume percent, e.g., in the range from about 0.01 to about 4 percent by volume acid based on the total volume of herbicide application composition and acidifying agent.

The herbicide compositions of the invention can be used for immediate and long-term, pre-and post-emergent control of a large variety of different forms of vegetation, particularly upon appropriate selection of the herbicide compound.

As an example, the MFC could be applied directly for controlling the growth of a plant, although this may include an unnecessarily potent concentration of the herbicide compound, and it can be difficult to uniformly apply a small amount of concentrated herbicide to a large area without dilution. An MFC would instead more likely be a product sold as a herbicide concentrate product, which would be a composition that includes a relatively high concentration of a herbicide compound as manufactured or packaged for sale, and which may be diluted prior to use to form a herbicide application composition, especially a microemulsion.

The MFC could be purchased by distributors or suppliers, or directly by consumers, either one of which could add water and other optional ingredients such as an acidifying agent or another type of herbicide or herbicide compound to the MFC. The additives could, for example, be added and mixed in a tank immediately prior to application.

In one embodiment of a distribution system, an MFC could be sold to farming product or nursery dealers, or the like, who could dilute the MFC with water and/or add other ingredients such as an acidifying agent. This could be particularly convenient if such a dealer normally kept on hand a stock of acidifying agent such as phosphoric acid or sulfuric acid, etc. The MFC or a microemulsion from the MFC, combined with an acidifying agent by the dealer, could be sold to an end consumer, who could use it as purchased or who could optionally further dilute the purchased composition or add other ingredients to the purchased composition such as an additional herbicide by tank mixing.

The herbicide compositions can be applied for immediate vegetation control by contact killing, by application of a herbicide application composition to plants. Herbicide application compositions can contain a useful amount of herbicide compound, based on factors of efficacy and safety, etc. Similarly, the amount of herbicide application composition applied to a plant or a field will be readily understood by those of skill, based, e.g., on desired efficacy and safety and environmental factors.

The particular amount of herbicide compound in any specific herbicide application composition will depend on factors as known and described above, and depending in particular on the identity of the specific herbicide compound. Advantageously, it has been found that certain preferred application compositions of the invention, especially those that include an acidifying agent, those that are applied with the herbicide compound in acid form, and in particular those that also have a pH that is below the pKa of the herbicide compound, can be applied at lower dosages (lower amounts of herbicide compound per plant or per acre) relative to other herbicide compositions containing the same herbicide compound, but not in the acid form or not at a pH lower than the pKa of the herbicide compound.

Examples of dosages of herbicide compound for application of a herbicide compound of preferred application compositions of the invention, especially herbicide compositions of the described pH, to a field, can be in the range from about 1/100 or 1/10 to about 10 pounds herbicide compound per acre, with dosages in the range from about 1/100 or 1/10 to about 6 pounds herbicide compound per acre being particularly useful, e.g., from about 0.03 to about 0.5 pounds per acre. More resistant plants or different field environments may require higher concentrations and/or higher dosage rates.

The preparation of herbicide application compositions suitable to apply useful dosages, based on the concentration of herbicide compound in a MFC or microemulsion will be well understood by those of ordinary skill.

The herbicide compositions can, as indicated, be applied using conventional aerial and field spray techniques in field applications. The herbicide compositions can also be applied by any other useful technique, such as by spot-application to undesired plant growth using a hand-held applicator, or the like.

Advantageously, herbicide compositions of the invention have been found to exhibit the additional advantages of being relatively non-volatile. The advantage of non-volatile herbicide compositions are self-evident to those of skill in the herbicide arts. A non-volatile herbicide composition has the advantage of not evolving, or evolving to a reduced degree, through the air, to inadvertently contact desired plant growth. In practical effect, this advantageous property allows the herbicide compositions of the invention to be applied to undesired plant growth in greater strength or in closer proximity to desired above-ground plant growth.

The herbicide compositions can be used for both immediate and long-term control of a large variety of vegetation including those usually found in agricultural fields such as bushes, scrub brush, vines, and other weeds.

Illustrative of vegetation that can be controlled by compositions of the invention, depending significantly on the identity of the herbicide compound, include: black mustard (brassica nigra), curly dock (rumex crispus), common groundsel (senecio vulgaris), pineapple weed (matricaria matricarioides), swamp smartweed (kelp) (polygonum coccineum), prickly lettus (lactuca scariola), lance-leaved groundcherry (physalis lanceifolia), annual sowthistle (sonchus oleraceus), london rocket (sisymbrium irio), common fiddleneck (amsinckia intermedia), hairy nightshade (solanum sarrachoides), shepherd's purse (capsella bursa-pastoris), sunflower (helianthus annus), common knotweed (polygonum aviculare), green amaranth (amaranthus hybridus), mare's tail (conyza canadensis), henbit (lamium amplexicaule), cocklebur (xanthium strumarium), cheeseweed (malva parviflora), lambsquarters (chenopodium album), puncture vine (tribulus terrestris) common purslane (portulaca oleracea), prostrate spurge (euphorbia supina), telegraph plant (heterotheca grandiflora), carpetweed (mollugo verticillata), yellow starthistle (centaurea solstitialis), milk thistle (silybum marianum), mayweed (anthemis cotula), burning nettle (urtica urens), fathen (atriplex patula), chickweed (stellaria media), scarlet pimpernel (anagallis arvensis) redroot pigweed (amaranthus retroflexus), minnerslettuce (montia perfoliata), turkey mullein (eremocarpus setigerus), nettle-leaf goosefoot (chenopodium murale), prostrate pigweed (amaranthus blitoides), silverleaf nightshade (solanum elaeagnifolium), hoary cress (cardaria draba), largeseed dodder (cuscuta indecora), California burclover (medicago polymorpha), horse purslane (trianthema portulacastrum), field bindweed (Iconvolvulus arvensis), Russian knapweed (centaurea repens), flax-leaved fleabane (conyza bonariensis), wild radish (raphanus sativus), tumble pigweed (amaranthus albus), stephanomeria (stephanomeria exigua), wild turnip (brassica campestris), buffalo goard (cucurbita foetidissima), common mullein (verbascum thapsus), dandelion (taraxacum officinale), Spanish thistle (xanthium spinosum), chicory (cichorium intybus), sweet anise (foeniculum vulgare), annual yellow sweetclover (melilotus indica), poison hemlock (conium maculatum), broadleaf filaree (erodium botrys), whitestem filaree (erodium moschatum), redstem filaree (erodium cicutarium), ivyleaf morning-glory (ipomea hederacea), shortpod mustard (brassica geniculata), buckhorn plantain (plantago lacenolata), sticky chickweed (cerastium viscosum), himalaya blackberry (rubus procerus), purslane speedwell (veronica peregrina), Mexican tea (chenopodium ambrosioides), Spanish clover (lotus purshianus), Australian brassbuttons (cotula australis), goldenrod (solidago californica), citron (citrullus lanatus), hedge mustard (sisymbrium orientale), black nightshade (solanum nodiflorum), Chinese thornapple (datura ferox), bristly ox tongue (picris echioides), bull thistle (cirsium vulgare), spiny sowthistle (sonchus asper), Tasmanian goosefoot (chenopodium pumilio), goosefoot (chenopodium botrys), wright groundcherry (physalis acutifolia), tomatillo groundcherry (physalis philadelphica), pretty spurge (euphorbia peplus), bitter apple (cucumis myriocarpus), indian tobacco (nicotiana bigelovii), common morning-glory (ipomoea purpurea), waterplantain (alisma triviale), smartweed (polygonum lapathifolium), mature sowthistle (sonchus asper), yellow nutsedge (cyperus esculentus), purple nutsedge (cyperus rotundus), lupine (lupinus formosus), and grasses of the family Gramineae such as annual rye grass, blue grass, water grass, barnyard grass, bermuda grass, fescue, mat grass, Johnson grass, and the like.

The ingredients of the herbicide compositions, e.g., the herbicide compound, surfactant, etc., can be selected in view of the type of control desired (i.e., pre-emergent or post-emergent) and the type of vegetation to be controlled according to the known attributes of the herbicide compound. Additionally, the herbicide compositions should be sufficiently chemically stable to assure that the herbicide compound retains its activity for the period of time required to manufacture, store, transport, and apply the herbicide compositions.

As mentioned, other herbicides or herbicide compositions can optionally be added to herbicide compositions of the invention, to provide broad range protection against certain varieties of plants. As a single example, glyphosate acid (N-phosphonomethylglycine acid) can be useful in combination with the herbicide compositions of the invention.

Glyphosate acid can be included in a herbicide composition in any useful amount, especially in a herbicide application composition in an amount of glyphosate that will provide complementary protection to the other herbicide compound of the herbicide composition. Also, the pH of the herbicide composition can preferably be below the pH of glyphosate acid, e.g., below about 2.6, so the glyphosate can exist in the acid form, preferably improving efficacy and avoiding precipitation.

MFCs of the invention can be prepared by any methods that will be understood as useful to dissolve a herbicide compound in acid form, into a surfactant. In general, the herbicide compound in acid form can typically be provided as a solid, but liquid oil soluble acid herbicide compounds are also typically available. An amount of the herbicide compound in acid form can be dissolved into a surfactant by selecting a proper surfactant or combination of surfactants (combinations of two or more surfactants will be referred to collectively herein as "surfactant"), each in useful amounts. As stated, exemplary MFCs can include from about 10 to about 40 parts by weight, e.g., from about 20 to about 35 parts by weight herbicide compound in acid form, and from about 60 to about 90, e.g., from about 65 to about 80 parts by weight surfactant. Useful amounts of herbicide compound in acid form and surfactant can of course be outside of these recited ranges, depending on preference, and on factors such as the solubility of the herbicide compound and whether an organic solvent or water is also present. Heat can optionally be used to facilitate dissolution of herbicide compound in surfactant. For example a mixture of herbicide compound and surfactant (with optional organic solvent) may be heated at a temperature, e.g., in the range from about 100F to about 200F, preferably from about 130 to about 150F, to facilitate dissolution of the herbicide compound in the surfactant. Heat may be applied until dissolution occurs. For example heating a 1 Kg lab batch for a period of from 30 minutes to 2 hours could generally be useful to dissolve a herbicide compound in acid form. It may be longer for a large production batch of 500–1000 Kg. Organic solvent or water may also be added to the mixture to facilitate dissolution, although it can be preferred to avoid the use of organic solvents. Agitation or other techniques may be used to encourage dissolution.

A skilled artisan will be able to determine whether a particular herbicide compound in acid form can be formed into an MFC by combining a herbicide compound in acid form with a single surfactant or a combination of surfactants, with optional heating, organic solvent, and agitation, to determine whether the surfactant is capable of dissolving the particular herbicide compound. A variety of different surfactants can be used, and a significant number of surfactant or surfactant combinations may have to be attempted to find one or a combination of surfactants that will be effective. Other techniques may also be used to facilitate or encourage dissolution, such as adjusting the speed and degree of agitation or by using slightly higher temperatures.

If other ingredients such as antifoaming agents are included in the MFC or microemulsion, such ingredients can be added as necessary, and in amounts and using techniques that will be well understood. If an acidifying agent is added, it can also be added at any stage of preparation of a herbicide composition, e.g., added to the MFC or by simple combining and mixing an acidifying agent into the microemulsion, e.g., by a dealer or by a consumer (farmer) with a tank mix. Likewise, if other herbicides or herbicide compounds are added to a herbicide composition of the invention, e.g., imidazolinone acid active herbicide compounds or glyphosate acid active herbicide compounds, these may be added by any of these or other methods, as will be appreciated, e.g., normally by simple combination mixing, either by a dealer, by a consumer (farmer) with a tank mix, or otherwise. See, for example, Assignee's copending U.S. Patent Application entitled "Herbicide Compositions Comprising Imidazolinone Acid, Methods of Preparation, and Methods of Use," having Attorney's docket number UAP0008/US/2, U.S. Ser. No. _____, filed on even date herewith, and incorporated herein by reference.

EXAMPLES

Below are specific microemulsion-forming concentrates of acid herbicides in surfactants. Nonionic, anionic, and cationic surfactants have been used in various ratios to make these microemulsion-forming concentrates.

2,4D Acid ME

Attempt to make 33.3%/wt 2,4-D. Formed an initial clear MFC which was diluted to 2% in water to form a microemulsion.
Formulation crystallized in 24 hours.
Tomadol 1-5     32.2%
Tomadol 1-7     32.8

-continued

Rhodafac RS 710     1.0
98% 2,4D Acid       34.0
2% dilution (2 parts MFC to 98 parts water) in 342 ppm is clear microemulsion, after 4 hrs.
Tomadol 1-5         36.1%
Tomadol 1-7         36.1
98% 2,4D Acid       27.8
2% dilution in 342 ppm is clear microemulsion, 4 hrs.

Fluroxypyr acid & 2,4-D Acid ME

Tomadol 1-5         13.9%
Tomadol 1-7         13.9
SAG 10 AF           0.1
Trymeen 6607        50.0    Cognis tallow amine ethoxylate
99% Fluroxypyr Acid 11.0
98% 2,4D Acid       11.1
2% dilution in 342 ppm opaque microemulsion @ 4 hrs 2,4D Acid ME Surfonic L12-6      71.3%   Huntsman 12 carbon 6 mole linear alcohol
SAG 10 AF           0.1
98% 2,4D Acid       28.6
5% dilution in 342 ppm is opaque microemulsion.
Tomadol 1-5         63.2%
Stepfac 8170        8.0     Stepan Phosphoric acid ester
SAG 10 AF           0.1
98% 2,4D Acid       28.6
5% dilution in 342 ppm is opaque microemulsion
Surfonic L12-6      63.3%
Surfonic PE-1218    8.0     Huntsman Phosphoric acid ester
SAG 10 AF           0.1
98% 2,4D Acid       28.6
5% dilution in 342 ppm is opaque microemulsion
Surfonic L12-6      61.3%   Huntsman linear alcohol
Surfonic PE-1218    10.0    Huntsman Phosphoric acid ester
SAG 10 AF           0.1
98% 2,4D Acid       28.6
2% dilution in 342 ppm is opaque microemulsion
Surfonic DDA6       61.3%   Huntsman branched alcohol ethoxylate
Surfonic PE-1218    10.0    Huntsman Phosphoric acid ester
SAG 10 AF           0.1
98% 2,4D Acid       28.6
2% dilution in 342 ppm is opaque microemulsion
Surfonic TDA6       63.3%   Huntsman tridecyl alcohol ethoxylate
Surfonic PE-1218    8.0     Huntsman Phosphoric acid ester
SAG 10 AF           0.1
98% 2,4D Acid       28.6
2% dilution in 342 ppm is opaque microemulsion
Tomadol 1-5         32.0    Tomah linear alcohol ethoxylates
Tomadol 1-7         31.30
Stepfac 8170        8.00    Stepan Phosphoric acid ester
SAG 10 AF           0.1
98% 2,4D Acid       28.6
5% dilution in 342 ppm is opaque microemulsion
Tomadol 1-5         32.0    Tomah linear alcohol ethoxylates
Tomadol 1-7         31.30
Stepfac 8170        8.00    Stepan Phosphoric acid ester
SAG 10 AF           0.1
98% 2,4D Acid       28.6
2% dilution in 342 ppm is opaque microemulsion Fluazifop Acid ME Surfonic L12-6      63.3%
Stepfac 8170        8.00    Stepan Phosphoric acid ester
SAG 10 AF           0.10
90% Fluzafop Acid   28.60

Fluroxypyr Acid ME, using organic solvent

Surfonic L12-6      24%/wt  linear alcohol nonionic
Surfonic T-15       45      tallow amine cationic
THFA #              10      solvent
99% fluroxypyr acid 21      active
tetrahydrofurfuryl alcohol -continued

Dicamba Acid ME

| | |
|---|---|
| Tomadol 1-5 | 32.1%/wt |
| Tomadol 1-7 | 30.9 |
| Stepfac 8170 | 8.0 |
| 97% Dicamba Acid | 29.0 |

MCPA Acid ME

| | |
|---|---|
| Tomadol 1-5 | 32.1%/wt |
| Tomadol 1-7 | 31.3 |
| Stepfac 8170 | 8.0 |
| 97% Dicamba Acid | 28.6 |

MCPP Acid ME

| | |
|---|---|
| Tomadol 1-5 | 32.1%/wt |
| Tomadol 1-7 | 31.3 |
| Stepfac 8170 | 8.0 |
| 97% Dicamba Acid | 28.6 |

Trichlorpyre Acid ME

| | |
|---|---|
| Tomadol 1-5 | 32.1%/wt |
| Tomadol 1-7 | 31.3 |
| Stepfac 8170 | 8.0 |
| 98.5% Triclopyr Acid | 28.5 |

2,4D Acid ME

| | | |
|---|---|---|
| Surfonic OP-70 | 63.3% | 7 mole octyl phenol |
| Stepfac 8170 | 8.0 | |
| 98% Dow 2,4D Acid | 28.6 | |
| SAG 10 Antifoam | 0.1 | |
| Tergitol NP6 | 63.3% | 6 mole nonyl phenol |
| Stepfac 8170 | 8.0 | |
| 98% Dow 2,4D Acid | 28.6 | |
| SAG 10 Antifoam | 0.1 | |
| Trylox 5902 | 63.3% | 16 mole castor oil ethoxylate |
| Stepfac 8170 | 8.0 | |
| 98% Dow 2,4D Acid | 28.6 | |
| SAG 10 Antifoam | 0.1 | |
| Span 20 | 35.3% | sorbitan laurate |
| Tween 80 | 28.0 | polysorbate 80 |
| Stepfac 8170 | 8.0 | |
| 98% Dow 2,4D Acid | 28.6 | |
| SAG 10 Antifoam | 0.1 | |
| Sophroflor 796P | 68.3% | ethoxylated tristerylphenol |
| Stepfac 8170 | 8.0 | |
| 98% Dow 2,4D Acid | 28.6 | |
| SAG 10 Antifoam | 0.1 | |

| | % |
|---|---|
| UHS 3 way acid mix 5108 MFC | |
| Surfonic L12-6, alcohol ethoxylate | 64.9 |
| Surfonic PE-1218, phosphate ester | 8.0 |
| 2,4D acid | 17.8 |
| MCPA acid | 7.6 |
| Dicamba acid | 1.6 |
| SAG 10, antifoam | 0.1 |
| pcc 1154, 1 lb/gal each 2,4D Acid, Fluroxypyr Acid MFC | |
| Tomadol 1-5, alcohol ethoxylate | 13.9 |
| Tomadol 1-7, alcohol ethoxylate | 13.9 |
| Surfonic T-15, tallow amine | 49.9 |
| Fluroxypyr acid | 11.1 |
| 2,4D acid | 11.1 |
| SAG 10 Antifoam | 0.1 |

PCC-1133 Microemulsion Formulation

| | | |
|---|---|---|
| 2,4-D Acid | 28.0 | 98% 2,4-acid technical flake |
| Tomadol 1-5 | 32.0 | 11 carbon 5 mole linear alcohol ethoxylate |
| Tomadol 1-7 | 32.3 | 11 carbon 7 mole linear alcohol ethoxylate |
| Rhodofac RS 710 | 8.0 | anionic, phosphate ester surfactant |
| SAG 10 Antifoam | 0.1 | |

The PCC-1133 microemulsion was prepared by adding surfactants to a mixing vessel and warming to 130F-150F. Antifoam and acid were added and mix in until clear, with the 2,4-D acid becoming dissolved in the surfactant, producing a MFC. A microemulsion was formed from the MFC by combining 2 ml MFC with 98 ml water with agitation.

Microemulsions were formed as follows:

Microemulsion-forming-concentrate was formed by adding dicamba to surfactant and mixing until dissolved with heat. Then, Engame and antifoam were mixed and added to the dicamba/surfactant MFC to form a microemulsion:

| | | |
|---|---|---|
| Neodol 1-5 | 20.00% | linear alcohol ethoxylate |
| 88% dicamba acid | 6.60 | |
| Engame | 73.30 | |
| Antifoam | 0.10 | |

(Engame is 9.6% glyphosate acid dissolved in a urea-sulfuric acid water base.)

In a method of using a composition containing herbicide acid (the combination of glyphosate acid and 2,4-D acid), surfactant, and acidifying agent, glyphosate acid was dissolved in surfactant and ingredients to produce a sulfuric acid/urea adduct, and that mixture was then used to solubilize 2,4-D in surfactant.

| | | |
|---|---|---|
| A. Vessel - Add in order listed keeping temperature below 130° F. | | |
| Water | 13.17% | |
| 93% sulfuric acid | 35.30 | |
| 97% glyphosate acid | 6.80 | |
| Urea | 20.30 | |
| Copper sulfate | 0.02 | corrosion inhibitor |
| Antifoam | 0.01 | |
| B. Vessel - Add in order listed keeping temperature between 130–150° F. | | |
| Tomadol 1-5 | 8.00 | 11 carbon 5 mole linear alcohol ethoxylate |
| Tomadol 1-7 | 8.00 | 11 carbon 7 mole linear alcohol ethoxylate |
| Rhodofac RS 710 | 1.70 | anionic, phosphate ester surfactant |
| 98% 2,4D Acid | 6.70 | |

The samples were clear. The solution of Vessel B was a microemulsion. Adding the solution of Vessel A to the solution of Vessel B with agitation formed a clear MFC product which when diluted, 2 parts MFC product to 98 parts water, formed an opaque microemulsion.

Glyphosate Acid in a ME

| | |
|---|---|
| Dipropylene glycol mono methyl ester | 5.00% |
| 40 mole castor oil ethoxylate | 10.00 |
| 98% 2,4D acid | 6.20 |
| 97% glyphosate acid | 6.20 |

-continued

| Glyphosate Acid in a ME | |
|---|---|
| Amads | 72.50 |
| Antifoam | 0.10 |

EXAMPLES 1–5

The following examples illustrate how microemulsions of the invention can be used to effect plant growth control, optionally with an acidifying agent.

Materials and Methods

Experiments were conducted to evaluate the efficacy of a variety of different types of herbicide formulations, including formulations from microemulsion-forming-concentrates, and to evaluate the effect of adding acids to the spray solution as an adjuvant (see Tables below). Each treatment in the experiment was replicated three times. An untreated control was also included in each experiment.

Experiment one was designed to identify useful acid concentrations of four acids when used with a 2,4-D acid (2,4-dichlorophenoxy acetic acid) formulation (PCC-1133), or a glyphosate (N-(phosphonomethyl)glycine) acid formulation (PCC-1168 suspension concentrate containing glyphosate acid), in a greenhouse. These treatments were compared to standard 2,4-D and glyphosate formulations (ROUNDUP ULTRA, SABER, SALVO), and an untreated control.

Experiment three considered the effect of adding acid adjuvants to PCC-1133, and compared the results to SALVO, SABER, and PCC-1133. Experiment four determined the effect of a variety of acid adjuvants: sulfuric acid, hydrochloric acid, nitric acid, glacial acetic acid, phosphoric acid, perchloric acid, perchloric acid, and polyphosphoric acid, on the efficacy of the 2,4-D acid formulation, PCC-1133, and the acid formulation alone, compared to ester and amine formulations of 2,4-D.

For each experiment conducted, greenhouse flats 26 cm$^2$ by 6 cm deep were filled with Metro Mix 200 potting soil (experiments one and two) or Metro Mix 350 (experiment three and four). The soil was pre-wetted before filling the flats. Six furrows were pressed into the soil in each flat using a custom designed form. Corn, tame oats, wheat, pinto beans, cotton, and sunflower were planted in each tray. Cottonseed was soaked for three days previous to planting to improve germination. Germination of the cottonseed was still unacceptable, however, and kochia was substituted in experiments 3 and 4. One species was planted in each of the six rows in each flat. Five seeds were planted in each row of corn, bean, and cotton, and sunflower. Six seeds were planted in each row of oat and wheat.

Kochia was sprinkled evenly along the row by hand. Each flat was covered with 2 cm of soil and placed in the greenhouse. Greenhouse conditions were 28/20 C day/night temperatures and 16/8 h day night periods. Light was supplemented with 400 W sodium halide lights.

The plants were allowed to germinate and grow in the greenhouse for 2 weeks and were then treated. Treatments were mixed using serial dilutions. In experiment one, the percent acid was reduced in each dilution by one half. In experiments 2 through 5 each dilution reduced the herbicide rate by one half (experiments 2 and 5 are not reported herein). Acid concentrations were calculated and mixed so that a treatment with one of the acids or LI-136 would have the same amount of acid as the treatment with PCC-1174. Therefore, a treatment designated 4% sulfuric acid would have the same amount of acid as a treatment with 4% PCC-1174.

After mixing in experiments one, four, and five, the pH of the spray solution of each treatment was measured with a, VWR Scientific model 8005 pH meter. The pH was measured to determine if the acid used or the amount of acid added was sufficient to lower the pH below the pKa of the acid herbicides used. The pKa of 2,4-D acid in the PCC-1133 is 2.87. The pKa of glyphosate acid in PCC-1168 is about 2.5 or 2.6.

At the time of treatment, crops were at the following stages: corn—2 to 3 lf, oat—2 to 3 lf, cotton—cotyledon, kochia—7 lf, bean—1st trifoliate, and sunflower—2 to 4 lf. Plants were treated using a greenhouse track sprayer equipped with an 8001E nozzle and calibrated to deliver 140 L ha-1 at the height of the crop canopy. Each treatment was simultaneously applied to three trays of plants, one for each replicate. After treatment, the plants were left in the head house to dry and then transferred to the greenhouse. Plants in each treatment were evaluated visually for injury 1 day, 1 week, and 2 weeks after treatment.

SUMMARY OF VARIABLES OF EXPERIMENTS 1, 3, and 4

Experiment 1

| Acid Treatment | Acid of each Volume v/v % | Herbicide | Herbicide Rate lb/A | Plants | Reps |
|---|---|---|---|---|---|
| PCC-1174 | 0 | PCC-1133 | 0.125 | dry beans | 3 |
| Sulfuric | 0.125 | PCC-1168 | 0.125 | wheat | 2 of standards |
| Phosphoric | 0.5 | Roundup Ultra | 0.125 | cotton | 2 of PCC-1133 and 1168 alone |
| LI-136 | 1 | Saber | 0.125 | corn | = 192 flats |
| | 2 | Salvo | 0.125 | sunflower | |
| | 4 | Untreated | 0.125 | oats | |

| Treatment | rates lb/A | Plants | Reps |
|---|---|---|---|

Experiment 3

| Salvo | 0.0313 | dry beans | 3 |
|---|---|---|---|
| SABER | 0.0625 | wheat | |
| PCC-1133 | 0.125 | kochia | |
| PCC-1133 + PCC-1174 (2%) | 0.025 | corn | |
| PCC-1133 + Sulfuric (2%) | 0.5 | sunflower | |
| PCC-1133 + Phosphoric (2%) | | oats | |
| PCC-1133 + LI-136 (2%) | | | |

Experiment 4

| PCC-1133 | 0.0313 | dry beans | 3 |
|---|---|---|---|
| PCC-1133 + Sulfuric (2%) | 0.0625 | wheat | |
| PCC-1133 + HCl (2%) | 0.125 | kochia | |
| PCC-1133 + Nitric (2%) | 0.025 | corn | |
| PCC-1133 + Acetic (2%) | 0.5 | sunflower | |
| PCC-1133 + Phosphoric (2%) | | oats | |
| PCC-1133 + Perchloric (2%) | | | |
| PCC-1133 + Polyphosphoric (2%) | | | |

Following are data that illustrate the efficacy of various herbicide compositions of Experiments 3 and 4. The injury caused by the herbicide treatment was rated visually. Plants were observed and compared to the untreated control. All the plants of each species in each replication were given a single rating. A rating of 0=no injury—the plants look the same as the untreated. A rating of 100=dead—usually highly necrotic, brown and no chance of producing seed.

SALVO® is a commercially available product of Platte Chemical Co. containing 5 lb 2,4-D acid equivalent/gallon as 2-ethyl-hexyl ester of 2,4-D SABER® is 2,4-D formulated as a dimethylamine salt (2,4-dichlorophenoxy dimethylamine salt), i.e., is a commercially available product of Platte Chemical Company containing 3.8 lb 2,4-D acid equivalent/gallon as dimethylamine salt.

RODEO is a soluble liquid water based formulation of IPA, glyphosate, and water, commercially available from MONSANTO, and was used according to the labeling instructions.

RODEO ULTRA is a glyphosate salt herbicide composition commercially available from MONSANTO, and was used according to the labeling instructions.

ENGAME is a soluble liquid water based formulation of glyphosate acid, urea, sulfuric acid, and water, commercially available from ENTEK, and was used according to the labeling instructions.

ROUNDUP and ROUNDUP ULTRA are commercially available IPA glyphosate salt and surfactant herbicide compositions.

| Chemical Name | 1-amino methanamide dihydrogen tetraoxosulfate, or sulfuric acid and urea |
|---|---|
| Molecular Formula | $NH_2C(OH)NHSO_4H_2$ |

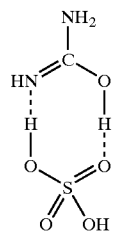

| INGREDIENT | %/WT |
|---|---|
| Water | 22.99 |
| 93% Sulfuric Acid | 48.65 |
| 99% Urea | 26.64 |
| Stepfac 8170 | 1.71 |
| SAG 10 Antifoam | 0.01 |

LI-136=blend of 50 wt. % 21-0-0 urea liquor and 50 wt percent of 72% phosphoric acid in water. The phrase "21-0-0 urea liquor" means a liquid that contains 21% by volume urea (nitrogen), 0% by volume phosphate (phosphorus), and 0% by volume potash (potassium).

Each of these acids were used as is and combined with the PCC-1133 or PCC-1168 to form a solution that contains 2 percent or 4 percent by volume of the acid solution, as indicated in the data tables, and such that the pH of the herbicide composition was below the pKa of the particular herbicide compound.

The ingredients of the herbicide compositions as applied are listed in the following data tables for Experiments 2–5, and were diluted in water and used at the rates indicated for herbicide ingredients and acidifying agents.

| | | Rate | Units | corn | tame oat | kochia | winter wheat | dry bean | sunflower |
|---|---|---|---|---|---|---|---|---|---|
| | DATA FOR EXPERIMENT 3 (TWO WEEK) | | | | | | | | |
| 1 | SALVO | .0313 | LB AE/A | 0.0 | 0.0 | 0.0 | 0.0 | 10.0 | 10.0 |
| 2 | SALVO | .0625 | LB AE/A | 0.0 | 0.0 | 0.0 | 0.0 | 30.0 | 30.0 |
| 3 | SALVO | 0.125 | LB AE/A | 0.0 | 0.0 | 0.0 | 0.0 | 60.0 | 40.0 |
| 4 | SALVO | 0.25 | LB AE/A | 0.0 | 0.0 | 0.0 | 0.0 | 90.0 | 90.0 |
| 5 | SALVO | 0.5 | LB AE/A | 0.0 | 0.0 | 0.0 | 0.0 | 90.0 | 90.0 |
| 6 | SABER | .0313 | LB AE/A | 0.0 | 0.0 | 0.0 | 0.0 | 5.0 | 0.0 |
| 7 | SABER | .0625 | LB AE/A | 0.0 | 0.0 | 0.0 | 0.0 | 10.0 | 5.0 |
| 8 | SABER | 0.125 | LB AE/A | 0.0 | 0.0 | 0.0 | 0.0 | 50.0 | 30.0 |
| 9 | SABER | 0.25 | LB AE/A | 0.0 | 0.0 | 0.0 | 0.0 | 80.0 | 70.0 |
| 10 | SABER | 0.5 | LB AE/A | 0.0 | 0.0 | 0.0 | 0.0 | 90.0 | 85.0 |
| 11 | PCC-1133 | .0313 | LB AE/A | 0.0 | 0.0 | 0.0 | 0.0 | 20.0 | 10.0 |
| 12 | PCC-1133 | .0625 | LB AE/A | 0.0 | 0.0 | 0.0 | 0.0 | 30.0 | 20.0 |
| 13 | PCC-1133 | 0.125 | LB AE/A | 0.0 | 0.0 | 0.0 | 0.0 | 50.0 | 50.0 |
| 14 | PCC-1133 | 0.25 | LB AE/A | 0.0 | 0.0 | 0.0 | 0.0 | 85.0 | 80.0 |
| 15 | PCC-1133 | 0.5 | LB AE/A | 0.0 | 0.0 | 0.0 | 0.0 | 90.0 | 90.0 |
| 16 | PCC-1133 PCC-1174 | .0313 2 | LB AE/A % V/V | 0.0 | 0.0 | 0.0 | 0.0 | 50.0 | 15.0 |
| 17 | PCC-1133 PCC-1174 | .0625 2 | LB AE/A % V/V | 0.0 | 0.0 | 0.0 | 0.0 | 50.0 | 30.0 |
| 18 | PCC-1133 PCC-1174 | 0.125 2 | LB AE/A % V/V | 0.0 | 0.0 | 0.0 | 0.0 | 70.0 | 60.0 |
| 19 | PCC-1133 PCC-1174 | 0.25 2 | LB AE/A % V/V | 0.0 | 0.0 | 0.0 | 0.0 | 95.0 | 95.0 |

-continued

| | | Rate | Units | | | | | | |
|---|---|---|---|---|---|---|---|---|---|
| 20 | PCC-1133 PCC-1174 | 0.5 2 | LB AE/A % V/V | 0.0 | 0.0 | 0.0 | 0.0 | 98.0 | 95.0 |
| 21 | PCC-1133 SULFURIC ACID | .0313 2 | LB AE/A % V/V | 0.0 | 0.0 | 0.0 | 0.0 | 35.0 | 20.0 |
| 22 | PCC-1133 SULFURIC ACID | .0625 2 | LB AE/A % V/V | 0.0 | 0.0 | 0.0 | 0.0 | 40.0 | 30.0 |
| 23 | PCC-1133 SULFURIC ACID | 0.125 2 | LB AE/A % V/V | 0.0 | 0.0 | 0.0 | 0.0 | 70.0 | 60.0 |
| 24 | PCC-1133 SULFURIC ACID | 0.25 2 | LB AE/A % V/V | 0.0 | 0.0 | 0.0 | 0.0 | 95.0 | 90.0 |
| 25 | PCC-1133 SULFURIC ACID | 0.5 2 | LB AE/A % V/V | 0.0 | 0.0 | 0.0 | 0.0 | 98.0 | 98.0 |
| 26 | PCC-1133 PHOSPHORIC ACID | .0313 2 | LB AE/A % V/V | 0.0 | 0.0 | 0.0 | 0.0 | 30.0 | 30.0 |
| 27 | PCC-1133 PHOSPHORIC ACID | .0625 2 | LB AE/A % V/V | 0.0 | 0.0 | 0.0 | 0.0 | 40.0 | 30.0 |
| 28 | PCC-1133 PHOSPHORIC ACID | 0.125 2 | LB AE/A % V/V | 0.0 | 0.0 | 0.0 | 0.0 | 65.0 | 60.0 |
| 29 | PCC-1133 PHOSPHORIC ACID | 0.25 2 | LB AE/A % V/V | 0.0 | 0.0 | 0.0 | 0.0 | 90.0 | 90.0 |
| 30 | PCC-1133 PHOSPHORIC ACID | 0.5 2 | LB AE/A % V/V | 0.0 | 0.0 | 0.0 | 0.0 | 95.0 | 97.0 |
| 31 | PCC-1133 LI-136 | .0313 2 | LB AE/A % V/V | 0.0 | 0.0 | 0.0 | 0.0 | 28.3 | 10.0 |
| 32 | PCC-1133 LI-136 | .0625 2 | LB AE/A % V/V | 0.0 | 0.0 | 0.0 | 0.0 | 50.0 | 40.0 |
| 33 | PCC-1133 LI-136 | 0.125 2 | LB AE/A % V/V | 0.0 | 0.0 | 0.0 | 0.0 | 70.0 | 60.0 |
| 34 | PCC-1133 LI-136 | 0.25 2 | LB AE/A % V/V | 0.0 | 0.0 | 0.0 | 0.0 | 90.0 | 90.0 |
| 35 | PCC-1133 LI-136 | 0.5 2 | LB AE/A % V/V | 0.0 | 0.0 | 0.0 | 0.0 | 95.0 | 90.0 |
| 36 | UNTREATED | | | 0.0 | 0.0 | 0.0 | 0.0 | 0.0 | 0.0 |

DATA FOR EXPERIMENT 4 (ONE WEEK)

| | | Rate | Units | corn | Tame oat | Kochia | winter wheat | dry bean | sunflower |
|---|---|---|---|---|---|---|---|---|---|
| 1 | PCC-1133 | .0313 | LB AE/A | 0.0 | 0.0 | 0.0 | 0.0 | 7.0 | 7.0 |
| 2 | PCC-1133 | .0625 | LB AE/A | 0.0 | 0.0 | 0.0 | 0.0 | 30.0 | 20.0 |
| 3 | PCC-1133 | 0.125 | LB AE/A | 0.0 | 0.0 | 0.0 | 0.0 | 50.0 | 40.0 |
| 4 | PCC-1133 | 0.25 | LB AE/A | 0.0 | 0.0 | 0.0 | 0.0 | 60.0 | 60.0 |
| 5 | PCC-1133 | 0.5 | LB AE/A | 0.0 | 0.0 | 0.0 | 0.0 | 80.0 | 80.0 |
| 6 | PCC-1133 SULFURIC ACID | .0313 2 | LB AE/A % V/V | 0.0 | 0.0 | 0.0 | 0.0 | 30.0 | 40.0 |
| 7 | PCC-1133 SULFURIC ACID | .0625 2 | LB AE/A % V/V | 0.0 | 0.0 | 0.0 | 0.0 | 40.0 | 40.0 |
| 8 | PCC-1133 SULFURIC ACID | 0.125 2 | LB AE/A % V/V | 0.0 | 0.0 | 0.0 | 0.0 | 80.0 | 60.0 |
| 9 | PCC-1133 SULFURIC ACID | 0.25 2 | LB AE/A % V/V | 0.0 | 0.0 | 0.0 | 0.0 | 80.0 | 85.0 |
| 10 | PCC-1133 SULFURIC ACID | 0.5 2 | LB AE/A % V/V | 0.0 | 0.0 | 0.0 | 0.0 | 95.0 | 90.0 |
| 11 | PCC-1133 HYDROCHLORIC ACID | .0313 2 | LB AE/A % V/V | 0.0 | 0.0 | 0.0 | 0.0 | 60.0 | 50.0 |
| 12 | PCC-1133 HYDROCHLORIC ACID | .0625 2 | LB AE/A % V/V | 0.0 | 0.0 | 0.0 | 0.0 | 55.0 | 55.0 |
| 13 | PCC-1133 HYDROCHLORIC ACID | 0.125 2 | LB AE/A % V/V | 0.0 | 0.0 | 0.0 | 0.0 | 65.0 | 70.0 |
| 14 | PCC-1133 HYDROCHLORIC ACID | 0.25 2 | LB AE/A % V/V | 0.0 | 0.0 | 0.0 | 0.0 | 90.0 | 85.0 |
| 15 | PCC-1133 HYDROCHLORIC ACID | 0.5 2 | LB AE/A % V/V | 0.0 | 0.0 | 0.0 | 0.0 | 97.0 | 95.0 |
| 16 | PCC-1133 NITRIC ACID | .0313 2 | % V/V LB AE/A | 0.0 | 0.0 | 0.0 | 0.0 | 30.0 | 30.0 |
| 17 | PCC-1133 NITRIC ACID | .0625 2 | % V/V LB AE/A | 0.0 | 0.0 | 0.0 | 0.0 | 60.0 | 60.0 |
| 18 | PCC-1133 NITRIC ACID | 0.125 2 | % V/V LB AE/A | 0.0 | 0.0 | 0.0 | 0.0 | 60.0 | 60.0 |
| 19 | PCC-1133 NITRIC ACID | 0.25 2 | % V/V LB AE/A | 0.0 | 0.0 | 0.0 | 0.0 | 83.3 | 85.0 |
| 20 | PCC-1133 NITRIC ACID | 0.5 2 | % V/V LB AE/A | 0.0 | 0.0 | 0.0 | 0.0 | 88.3 | 90.0 |
| 21 | PCC-1133 GLACIAL ACETIC ACID | .0313 2 | % V/V LB AE/A | 0.0 | 0.0 | 0.0 | 0.0 | 40.0 | 20.0 |
| 22 | PCC-1133 GLACIAL ACETIC ACID | .0625 2 | % V/V LB AE/A | 0.0 | 0.0 | 0.0 | 0.0 | 50.0 | 30.0 |

-continued

| | | Rate | Units | | | | | | |
|---|---|---|---|---|---|---|---|---|---|
| 23 | PCC-1133<br>GLACIAL ACETIC ACID | 0.125<br>2 | % V/V<br>LB AE/A | 0.0 | 0.0 | 0.0 | 0.0 | 65.0 | 70.0 |
| 24 | PCC-1133<br>GLACIAL ACETIC ACID | 0.25<br>2 | % V/V<br>LB AE/A | 0.0 | 0.0 | 0.0 | 0.0 | 65.0 | 70.0 |
| 25 | PCC-1133<br>GLACIAL ACETIC ACID | 0.5<br>2 | % V/V<br>% V/V | 0.0 | 0.0 | 0.0 | 0.0 | 85.0 | 80.0 |
| 26 | PCC-1133<br>PHOSPHORIC ACID | .0313<br>2 | LB AE/A<br>% V/V | 0.0 | 0.0 | 0.0 | 0.0 | 50.0 | 40.0 |
| 27 | PCC-1133<br>PHOSPHORIC ACID | .0625<br>2 | LB AE/A<br>% V/V | 0.0 | 0.0 | 0.0 | 0.0 | 50.0 | 40.0 |
| 28 | PCC-1133<br>PHOSPHORIC ACID | 0.125<br>2 | LB AE/A<br>% V/V | 0.0 | 0.0 | 0.0 | 0.0 | 85.0 | 60.0 |
| 29 | PCC-1133<br>PHOSPHORIC ACID | 0.25<br>2 | LB AE/A<br>% V/V | 0.0 | 0.0 | 0.0 | 0.0 | 90.0 | 80.0 |
| 30 | PCC-1133<br>PHOSPHORIC ACID | 0.5<br>2 | LB AE/A<br>% V/V | 0.0 | 0.0 | 0.0 | 0.0 | 95.0 | 90.0 |
| 31 | PCC-1133<br>PERCHLORIC ACID | .0313<br>2 | LB AE/A<br>% V/V | 0.0 | 0.0 | 0.0 | 0.0 | 30.0 | 30.0 |
| 32 | PCC-1133<br>PERCHLORIC ACID | .0625<br>2 | LB AE/A<br>% V/V | 0.0 | 0.0 | 0.0 | 0.0 | 40.0 | 30.0 |
| 33 | PCC-1133<br>PERCHLORIC ACID | 0.125<br>2 | LB AE/A<br>% V/V | 0.0 | 0.0 | 0.0 | 0.0 | 50.0 | 60.0 |
| 34 | PCC-1133<br>PERCHLORIC ACID | 0.25<br>2 | LB AE/A<br>% V/V | 0.0 | 0.0 | 0.0 | 0.0 | 75.0 | 60.0 |
| 35 | PCC-1133<br>PERCHLORIC ACID | 0.5<br>2 | LB AE/A<br>% V/V | 0.0 | 0.0 | 0.0 | 0.0 | 85.0 | 70.0 |
| 36 | PCC-1133<br>POLYPHOSPHORIC ACID | .0313<br>2 | LB AE/A<br>% V/V | 0.0 | 0.0 | 0.0 | 0.0 | 50.0 | 40.0 |
| 37 | PCC-1133<br>POLYPHOSPHORIC ACID | .0625<br>2 | LB AE/A<br>% V/V | 0.0 | 0.0 | 0.0 | 0.0 | 60.0 | 40.0 |
| 38 | PCC-1133<br>POLYPHOSPHORIC ACID | 0.125<br>2 | LB AE/A<br>% V/V | 0.0 | 0.0 | 0.0 | 0.0 | 60.0 | 60.0 |
| 39 | PCC-1133<br>POLYPHOSPHORIC ACID | 0.25<br>2 | LB AE/A<br>% V/V | 0.0 | 0.0 | 0.0 | 0.0 | 85.0 | 80.0 |
| 40 | PCC-1133<br>POLYPHOSPHORIC ACID | 0.5<br>2 | LB AE/A<br>% V/V | 0.0 | 0.0 | 0.0 | 0.0 | 90.0 | 90.0 |
| 41 | SABER | .0313 | LB AE/A | 0.0 | 0.0 | 0.0 | 0.0 | 10.0 | 5.0 |
| 42 | SABER | .0625 | LB AE/A | 0.0 | 0.0 | 0.0 | 0.0 | 30.0 | 10.0 |
| 43 | SABER | 0.125 | LB AE/A | 0.0 | 0.0 | 0.0 | 0.0 | 50.0 | 20.0 |
| 44 | SABER | 0.25 | LB AE/A | 0.0 | 0.0 | 0.0 | 0.0 | 60.0 | 60.0 |
| 45 | SABER | 0.5 | LB AE/A | 0.0 | 0.0 | 0.0 | 0.0 | 60.0 | 60.0 |
| 46 | UNTREATED | | | 0.0 | 0.0 | 0.0 | 0.0 | 0.0 | 0.0 |

DATA FOR EXPERIMENT 4 (TWO WEEK)

| | | Rate | Units | corn | tame oat | kochia | winter wheat | dry bean | sunflower |
|---|---|---|---|---|---|---|---|---|---|
| 1 | PCC-1133 | .0313 | LB AE/A | 0.0 | 0.0 | 0.0 | 0.0 | 0.0 | 5.0 |
| 2 | PCC-1133 | .0625 | LB AE/A | 0.0 | 0.0 | 0.0 | 0.0 | 40.0 | 20.0 |
| 3 | PCC-1133 | 0.125 | LB AE/A | 0.0 | 0.0 | 0.0 | 0.0 | 50.0 | 40.0 |
| 4 | PCC-1133 | 0.25 | LB AE/A | 0.0 | 0.0 | 0.0 | 0.0 | 70.0 | 70.0 |
| 5 | PCC-1133 | 0.5 | LB AE/A | 0.0 | 0.0 | 0.0 | 0.0 | 85.0 | 85.0 |
| 6 | PCC-1133<br>SULFURIC ACID | .0313<br>2 | LB AE/A<br>% V/V | 0.0 | 0.0 | 0.0 | 0.0 | 50.0 | 40.0 |
| 7 | PCC-1133<br>SULFURIC ACID | .0625<br>2 | LB AE/A<br>% V/V | 0.0 | 0.0 | 0.0 | 0.0 | 60.0 | 60.0 |
| 8 | PCC-1133<br>SULFURIC ACID | 0.125<br>2 | LB AE/A<br>% V/V | 0.0 | 0.0 | 0.0 | 0.0 | 80.0 | 70.0 |
| 9 | PCC-1133<br>SULFURIC ACID | 0.25<br>2 | LB AE/A<br>% V/V | 0.0 | 0.0 | 0.0 | 0.0 | 90.0 | 80.0 |
| 10 | PCC-1133<br>SULFURIC ACID | 0.5<br>2 | LB AE/A<br>% V/V | 0.0 | 0.0 | 0.0 | 0.0 | 95.0 | 88.3 |
| 11 | PCC-1133<br>HYDROCHLORIC ACID | .0313<br>2 | LB AE/A<br>% V/V | 0.0 | 0.0 | 0.0 | 0.0 | 60.0 | 50.0 |
| 12 | PCC-1133<br>HYDROCHLORIC ACID | .0625<br>2 | LB AE/A<br>% V/V | 0.0 | 0.0 | 0.0 | 0.0 | 60.0 | 50.0 |
| 13 | PCC-1133<br>HYDROCHLORIC ACID | 0.125<br>2 | LB AE/A<br>% V/V | 0.0 | 0.0 | 0.0 | 0.0 | 70.0 | 70.0 |
| 14 | PCC-1133<br>HYDROCHLORIC ACID | 0.25<br>2 | LB AE/A<br>% V/V | 0.0 | 0.0 | 0.0 | 0.0 | 90.0 | 85.0 |
| 15 | PCC-1133<br>HYDROCHLORIC ACID | 0.5<br>2 | LB AE/A<br>% V/V | 0.0 | 0.0 | 0.0 | 0.0 | 99.0 | 97.0 |
| 16 | PCC-1133<br>NITRIC ACID | .0313<br>2 | % V/V<br>LB AE/A | 0.0 | 0.0 | 0.0 | 0.0 | 40.0 | 30.0 |
| 17 | PCC-1133<br>NITRIC ACID | .0625<br>2 | % V/V<br>LB AE/A | 0.0 | 0.0 | 0.0 | 0.0 | 60.0 | 60.0 |
| 18 | PCC-1133<br>NITRIC ACID | 0.125<br>2 | % V/V<br>LB AE/A | 0.0 | 0.0 | 0.0 | 0.0 | 60.0 | 60.0 |

-continued

| | | | | | | | | | |
|---|---|---|---|---|---|---|---|---|---|
| 19 | PCC-1133 | 0.25 | % V/V | 0.0 | 0.0 | 0.0 | 0.0 | 90.0 | 85.0 |
| | NITRIC ACID | 2 | LB AE/A | | | | | | |
| 20 | PCC-1133 | 0.5 | % V/V | 0.0 | 0.0 | 0.0 | 0.0 | 93.0 | 90.0 |
| | NITRIC ACID | 2 | LB AE/A | | | | | | |
| 21 | PCC-1133 | .0313 | % V/V | 0.0 | 0.0 | 0.0 | 0.0 | 50.0 | 30.0 |
| | GLACIAL ACETIC ACID | 2 | LB AE/A | | | | | | |
| 22 | PCC-1133 | .0625 | % V/V | 0.0 | 0.0 | 0.0 | 0.0 | 50.0 | 30.0 |
| | GLACIAL ACETIC ACID | 2 | LB AE/A | | | | | | |
| 23 | PCC-1133 | 0.125 | % V/V | 0.0 | 0.0 | 0.0 | 0.0 | 65.0 | 65.0 |
| | GLACIAL ACETIC ACID | 2 | LB AE/A | | | | | | |
| 24 | PCC-1133 | 0.25 | % V/V | 0.0 | 0.0 | 0.0 | 0.0 | 70.0 | 70.0 |
| | GLACIAL ACETIC ACID | 2 | LB AE/A | | | | | | |
| 25 | PCC-1133 | 0.5 | % V/V | 0.0 | 0.0 | 0.0 | 0.0 | 95.0 | 90.0 |
| | GLACIAL ACETIC ACID | 2 | % V/V | | | | | | |
| 26 | PCC-1133 | .0313 | LB AE/A | 0.0 | 0.0 | 0.0 | 0.0 | 60.0 | 50.0 |
| | PHOSPHORIC ACID | 2 | % V/V | | | | | | |
| 27 | PCC-1133 | .0625 | LB AE/A | 0.0 | 0.0 | 0.0 | 0.0 | 60.0 | 50.0 |
| | PHOSPHORIC ACID | 2 | % V/V | | | | | | |
| 28 | PCC-1133 | 0.125 | LB AE/A | 0.0 | 0.0 | 0.0 | 0.0 | 85.0 | 70.0 |
| | PHOSPHORIC ACID | 2 | % V/V | | | | | | |
| 29 | PCC-1133 | 0.25 | LB AE/A | 0.0 | 0.0 | 0.0 | 0.0 | 90.0 | 80.0 |
| | PHOSPHORIC ACID | 2 | % V/V | | | | | | |
| 30 | PCC-1133 | 0.5 | LB AE/A | 0.0 | 0.0 | 0.0 | 0.0 | 97.0 | 93.0 |
| | PHOSPHORIC ACID | 2 | % V/V | | | | | | |
| 31 | PCC-1133 | .0313 | LB AE/A | 0.0 | 0.0 | 0.0 | 0.0 | 40.0 | 30.0 |
| | PERCHLORIC ACID | 2 | % V/V | | | | | | |
| 32 | PCC-1133 | .0625 | LB AE/A | 0.0 | 0.0 | 0.0 | 0.0 | 50.0 | 30.0 |
| | PERCHLORIC ACID | 2 | % V/V | | | | | | |
| 33 | PCC-1133 | 0.125 | LB AE/A | 0.0 | 0.0 | 0.0 | 0.0 | 50.0 | 60.0 |
| | PERCHLORIC ACID | 2 | % V/V | | | | | | |
| 34 | PCC-1133 | 0.25 | LB AE/A | 0.0 | 0.0 | 0.0 | 0.0 | 75.0 | 70.0 |
| | PERCHLORIC ACID | 2 | % V/V | | | | | | |
| 35 | PCC-1133 | 0.5 | LB AE/A | 0.0 | 0.0 | 0.0 | 0.0 | 85.0 | 80.0 |
| | PERCHLORIC ACID | 2 | % V/V | | | | | | |
| 36 | PCC-1133 | .0313 | LB AE/A | 0.0 | 0.0 | 0.0 | 0.0 | 50.0 | 20.0 |
| | POLYPHOSPHORIC ACID | 2 | % V/V | | | | | | |
| 37 | PCC-1133 | .0625 | LB AE/A | 0.0 | 0.0 | 0.0 | 0.0 | 55.0 | 40.0 |
| | POLYPHOSPHORIC ACID | 2 | % V/V | | | | | | |
| 38 | PCC-1133 | 0.125 | LB AE/A | 0.0 | 0.0 | 0.0 | 0.0 | 65.0 | 60.0 |
| | POLYPHOSPHORIC ACID | 2 | % V/V | | | | | | |
| 39 | PCC-1133 | 0.25 | LB AE/A | 0.0 | 0.0 | 0.0 | 0.0 | 85.0 | 85.0 |
| | POLYPHOSPHORIC ACID | 2 | % V/V | | | | | | |
| 40 | PCC-1133 | 0.5 | LB AE/A | 0.0 | 0.0 | 0.0 | 0.0 | 91.7 | 90.0 |
| | POLYPHOSPHORIC ACID | 2 | % V/V | | | | | | |
| 41 | SABER | .0313 | LB AE/A | 0.0 | 0.0 | 0.0 | 0.0 | 10.0 | 5.0 |
| 42 | SABER | .0625 | LB AE/A | 0.0 | 0.0 | 0.0 | 0.0 | 20.0 | 10.0 |
| 43 | SABER | 0.125 | LB AE/A | 0.0 | 0.0 | 0.0 | 0.0 | 50.0 | 50.0 |
| 44 | SABER | 0.25 | LB AE/A | 0.0 | 0.0 | 0.0 | 0.0 | 70.0 | 70.0 |
| 45 | SABER | 0.5 | LB AE/A | 0.0 | 0.0 | 0.0 | 0.0 | 75.0 | 75.0 |
| 46 | UNTREATED | | | 0.0 | 0.0 | 0.0 | 0.0 | 0.0 | 0.0 |

We claim:

1. A microemulsion-forming-concentrate comprising herbicide compound in acid form and surfactant, wherein the concentrate can be combined with water to form a microemulsion.

2. The concentrate of claim 1 wherein the herbicide compound in acid form is chosen from the group consisting of: a phenoxy herbicide, a pyridine herbicide, a benzoic acid herbicide, a quinolinic acid herbicide, an aryloxy phenoxy propionic acid herbicide, and combinations thereof.

3. The concentrate of claim 1 wherein the herbicide acid is selected from the group consisting of 2,4-dichlorophenoxyacetic acid, dicamba acid (3,6-dichloro-O-anisic acid), 4-methyl-4-chlorophenoxyacetic acid, 2(-2-methyl-4-chlorophenoxy)propionic acid, 3,5,6-trichloro-2-pyridyloxyacetic acid (triclopyr acid), fluazifop acid, [(4-amino-3,5-dichloro-6-fluoro-2-pyridinyl)oxy]acetic acid (fluroxypyr acid), and combinations thereof.

4. The concentrate of claim 1 comprising herbicide compound in acid form, surfactant, and essentially no organic solvent.

5. The concentrate of claim 1 comprising herbicide compound in acid form, surfactant, and essentially no water.

6. The concentrate of claim 1 consisting essentially of herbicide compound in acid form and surfactant.

7. The concentrate of claim 1 comprising from about 10 to about 40 parts by weight herbicide compound in acid form, and from about 60 to about 90 parts by weight surfactant.

8. The concentrate of claim 1 comprising from about 20 to about 35 parts by weight herbicide compound in acid form, and from about 65 to about 80 parts by weight surfactant.

9. The concentrate of claim 1 wherein the surfactant is selected from the group consisting of an anionic surfactant, a cationic surfactant, a non-ionic surfactant, and combinations thereof.

10. The concentrate of claim 1 comprising surfactant selected from the group consisting of a non-ionic linear or branched alcohol ethoxylate surfactant, an anionic phosphoric acid ester surfactant, a cationic ethoxylated tallow amine surfactant, and combinations thereof.

11. The concentrate of claim 1 comprising surfactant selected from the group consisting of: an ethoxylated linear alcohol; an ethoxylated amine; an ethoxylated amide; a phosphate ester; a branched alcohol ethoxylate; an ethoxylated alkyl phenol; an ethoxylated fatty acid; a sorbitan laurate; a sorbitan oleate; a propylated, ethoxylated fatty acid, alcohol, or alkyl phenol; and combinations thereof.

12. The concentrate of claim 1 consisting essentially of:

from about 65 to about 80 parts by weight surfactant, from about 20 to about 35 parts by weight herbicide compound in acid form selected from the group consisting of 2,4-dichlorophenoxyacetic acid, dicamba acid (3,6-dichloro-O-anisic acid), 4-methyl-4-chlorophenoxyacetic acid, 2(-2-methyl-4-chlorophenoxy)propionic acid, 3,5,6-trichloro-2-pyridyloxyacetic acid (triclopyr acid), fluazifop acid, [(4-amino-3,5-dichloro-6-fluoro-2-pyridinyl)oxy] acetic acid (fluoroxypyr acid), and combinations thereof, and no added water or added organic solvent.

13. The concentrate of claim 1 wherein the concentrate contains from about 25 to about 35 parts by weight 2,4-dichlorophenoxyacetic acid, and from about 65 to about 75 parts by weight surfactant selected from the group consisting of a linear alcohol ethoxylate, a phosphate ester, and combinations thereof.

14. A microemulsion comprising a microemulsion-forming-concentrate comprising herbicide compound in acid form, surfactant, and water.

15. The microemulsion of claim 14 comprising from about 0.05 to about 7 volume percent microemulsion-forming-concentrate comprising from about 10 to about 40 parts by weight herbicide compound in acid form and from about 60 to about 90 parts by weight surfactant, and from about 93 to about 99.95 volume percent water.

16. The microemulsion of claim 15 further comprising acidifying agent.

17. A method of preparing herbicide, the method comprising:

preparing a microemulsion-forming-concentrate comprising herbicide compound in acid form and surfactant, preparing a microemulsion from the microemulsion-forming-concentrate by diluting the microemulsion with an aqueous solution, the microemulsion comprising herbicide compound in acid form.

18. The method of claim 17 further comprising applying the herbicide composition to a plant to control plant growth, while the herbicide compound is in acid form.

19. The method of claim 17 wherein the aqueous solution is a liquid selected from the group consisting of water, a concentrated aqueous acid, and a dilute aqueous acid.

20. A method of preparing a microemulsion-forming-concentrate, the method comprising combining herbicide compound in acid form with surfactant, with optional heat and optional agitation, to produce a microemulsion-forming-concentrate that can be combined with water to form a microemulsion.

21. A method of preparing a microemulsion, the method comprising:

preparing a microemulsion-forming-concentrate by a method comprising combining herbicide compound in acid form with surfactant to produce a microemulsion-forming-concentrate that can be combined with water to form a microemulsion, and combining the microemulsion-forming-concentrate with water to form a microemulsion.

22. The method of claim 21 comprising combining from about 0.05 to about 7 parts by volume microemulsion-forming-concentrate with from about 93 to about 99.95 parts by weight water.

23. The method of claim 21 further comprising adding an acidifying agent to the microemulsion-forming-concentrate.

24. The method of claim 21 further comprising adding an acidifying agent to the microemulsion.

* * * * *

UNITED STATES PATENT AND TRADEMARK OFFICE
CERTIFICATE OF CORRECTION

PATENT NO. : 6,803,345 B2  Page 1 of 1
APPLICATION NO. : 10/103455
DATED : October 12, 2004
INVENTOR(S) : Herold et al.

It is certified that error appears in the above-identified patent and that said Letters Patent is hereby corrected as shown below:

Col. 12, line 8, "_____," should be --10/102,799--.

Col. 12, line 14, "_____," should be --10/103,493--.

Col. 17, line 50, "_____," should be --10/103,519--.

Col. 23, before line 25, please add:

Acidifying Agents
HCl 37%
Nitric 70%
Glacial Acetic 100%
Perchloric 60%
Polyphosphoric 100%

PCC-1174
Commercially available as "AMADS," which is urea and $H_2SO_4$ in water:

Signed and Sealed this

Eighth Day of August, 2006

JON W. DUDAS
*Director of the United States Patent and Trademark Office*